United States Patent
Yokoyana et al.

(10) Patent No.: US 6,548,737 B1
(45) Date of Patent: Apr. 15, 2003

(54) TRANSGENIC MICE DEFICIENT IN NATURAL KILLER CELLS

(75) Inventors: Wayne M. Yokoyana, Ladue, MO (US); Sungjin Kim, Clayton, MO (US)

(73) Assignee: Barnes-Jewish Hospital, St. Louis, MO (US)

( * ) Notice: Subject to any disclaimer, the term of this patent is extended or adjusted under 35 U.S.C. 154(b) by 0 days.

(21) Appl. No.: 09/312,454

(22) Filed: May 14, 1999

Related U.S. Application Data

(60) Provisional application No. 60/085,568, filed on May 15, 1998.

(51) Int. Cl.[7] ............ A01K 67/027; G01N 33/00; C12N 15/00; C12N 15/63; C12N 15/85

(52) U.S. Cl. ............ 800/18; 3/22; 3/25; 435/320.1; 435/325; 435/455

(58) Field of Search ............ 800/3, 9, 14, 18, 800/22, 25; 435/320.1, 325, 455; 530/350

(56) References Cited

U.S. PATENT DOCUMENTS

| | | | |
|---|---|---|---|
| 4,736,866 A | 4/1988 | Leder et al. | 800/10 |
| 5,175,383 A | 12/1992 | Leder et al. | 800/10 |
| 5,530,179 A | 6/1996 | Terhorst et al. | 800/3 |
| 5,602,305 A | 2/1997 | Pober et al. | 800/11 |
| 5,698,763 A | 12/1997 | Weissman et al. | 800/18 |
| 5,718,883 A | 2/1998 | Harlan et al. | 424/9.2 |

OTHER PUBLICATIONS

Cantorna et al, 1995, Euro. J. Immunol., 25: 1673–1679.*
Simon et al, 1997, J. Exp. Med., 186: 1781–1786.*
Ebert et al, 1988, Mol. Endocrinol., 2: 277–283.*
Hammer et al, 1986, J. Anim. Sci., 63: 269–278.*
Houdebine et al, 1994, J. Biotechnol., 34: 269–287.*
Kappel et al, 1992, Cur. Opin. Biotech., 3: 548–553.*
Moreadith et al, 1997, J. Mol. Med., 75: 208–216.*
Mullins et al, 1996, J. Clin. Invest., 98: S37–40.*
Seamark et al, 1994, Reprod. Fert. Devolop., 6: 653–657.*
Strojek et al, 1988, Genetic Engineering: Principles and methods, Plenum Press, 10: 221–246.*
Wall et al, 1996, Theriogenology, 45: 57–68.*
Herberman, R.B., et al., "Natural Cytotoxic Reactivity of Mouse Lymphoid Cells Against Syngeneic and Allogeneic Tumors", Int. J. Cancer, 1975, vol. 16, pp. 216–229.
Kiessling, R., et al, "Natural Killer Cells in the Mouse I. Cytotoxic Cells with Specificity for Mouse Moloney Leukemia Cell: Specificity and Distribution According to Genotype", Eur. J. Immunol., 1975, vol. 5, p. 112.
Hackett, J., Jr., M. Bennet, V. Kumar, "Origin and Differentiation of Natural Killer Cells. I. Characteristics of a Transplantable NK Cell Precursor", J. Immunol., 1985, vol. 134, pp. 3731–3738.

Hackett, J., Jr., G.C. Bosma, M.J. Bosma, M. Bennett, V. Kumar, "Transplantable Progenitors of Natural Killer Cells are Distinct From Those of T and B Lymphocytes", Proc. Natl. Acad. Sci., U.S.A., 1986, vol. 83: pp. 3427–3431.
Suttles, J., G.A. Schwarting, R.D. Stout, Flow Cytometricanalysis Reveals the Presence of Asialo GM1 on the Surface Membrane of Alloimmune Cytotoxic T Lymphocytes, J. Immunol., 1986, vol. 136: pp. 1586–1591.
Koo, G.C., F.J. Dumont, M. Tutt, J. Hackett, Jr., V. Kumar, The NK–1.1(–) Mouse: A Model to Study Differentiation of Murine NK Cells, J. Immunol., 1986, vol. 137: pp. 3742–3747.
Sentman, C.L., J. Hackett, Jr., V. Kumar, M. Bennett, "Identification of a Subset of Murine Natural Killer Cells that Mediates Rejection of Hh–1d but not Hh–1b Bone Marrow Grafts", J. Exp. Med., 1989, vol. 170, pp. 191–202.
Trinchieri, G., "Biology of Natural Killer Cells", Adv. Immunol., 1989, vol. 47: pp. 187–376.
Yokoyama, W.M., L.B. Jacobs, O. Kanagawa, E.M. Shevach, D.I. Cohen, "A Murine T Lymphocyte Antigen Belongs to a Supergene Family of Type II Integral Membrane Proteins", J.Immunol., 1989, vol. 143, pp. 1379–1386.
Biron, C.A., K.S. Byron, J.L. Sullivan, "Severe Herpesvirus Infections in an Adolescent Without Natural Killer Cells", N. Engl. J. Med., 1989, vol. 320, pp. 1731–1735.
Scalzo A.A., et al, "CMV–1, A Genetic Locus that Controls Murine Cytomegalovirus Replication in the Spleen", J. Exp. Med., May 1, 1990, vol. 171(5), pp. 1469–1483.
Karlhoffer, F.M., W.M. Yokoyama, "Stimulation of the Murine Natural Killer (NK) Cells by a Monoclonal Antibody Specific for the NK1.1 Antigen. IL–2–Activated NK Cells Possess Additional Specific Stimulation Pathways", J. Immunol., 1991, vol. 146, pp. 3662–3673.
Bix, M., N.S. Liao, M. Zijlstra, J. Loring, R. Jaenisch, D. Raulet, "Rejection of Class I MHC–Deficient Haemopoietic Cells by Irradiated MHC–Matched Mice", Nature, 1991, vol. 349, pp. 329–331.
Kitamura, D., J. Roes, R. Kuhn, K. Rajewsky, "A Bcell–Deficient Mouse by Targeted Disruption of the Membrane Exon of the Immunoglobulin Mu Chain Gene", Nature, 1991, vol. 350, pp. 423–426.

(List continued on next page.)

Primary Examiner—Deborah Crouch
Assistant Examiner—Peter Paras, Jr.
(74) Attorney, Agent, or Firm—Sonnenschein Nath & Rosenthal

(57) ABSTRACT

A mouse is provided which is selectively deficient in natural killer cells. Also provided are methods for producing the mouse. Additionally, mice which are deficient in natural killer cells and B cells, natural killer cells and T cells, and natural killer cells, T cells, and B cells are provided, along with methods for making these mice. Methods of using these mice to: produce an animal containing human tissue, evaluate the effects of a composition on human tissue, determine whether a human disease is caused by a pathogenic agent, and study natural killer cells are also provided.

13 Claims, 10 Drawing Sheets

OTHER PUBLICATIONS

Shinkai, Y., G. Rathbun, K.P. Lam, E.M. Oltz, V. Stewart, M. Mendelsohn, J. Charron, M. Datta, F. Young, A.M. Stall, et al, "RAG–2 Deficient Mice Lack Mature Lymphocytes Owing to Inability to Initiate V(D)J Rearrangments", Cell, 1992, vol. 68, pp. 855–867.

Mombaerts, P., J. Iacomini, R.S. Johnson, K. Herrup, S. Tonegawa, V.E. Papaioannou, "RAG–1–Deficient Mice Have No Mature B and T Lymphocytes", Cell, 1992, vol. 68, pp. 869–877.

Hershberger, R.J., H.K. Gershenfeld, I.L. Weissman, L. Su, "Genomic Organization of the Mouse Granzyme A Gene. Two mRNAs Encode the Same Mature Granzyme A With Different Leader Peptides", J. Biol. Chem., 1992, vol. 267, pp. 25488–25493.

Mombaerts, P., A.R. Clarke, M.A. rudnicki, J. Iacomini, S. Itohara, J.J. Lafaille, L. Wang, Y. Ichikawa, R. Jaenisch, M.L. Hooper, et al, "Mutations in T–Cell Antigen Receptor Genes Alpha and Beta Block Thymocyte Development at Different Stages", Nature, 1992, vol. 360, pp. 225–231.

Locksley, R.M., "Interleukin 12 in Host Defense Against Microbial Pathogens", Natl. Acad. Sci. USA, 1993, vol;. 90, pp. 5879–5880.

Bancroft, G. J., "The Role of Natural Killer Cells in Innate Resistance to Infection", Curr. Opin, Immunol., 1993, vol. 5: pp. 503–510.

Shultz, L.D., P.A. Schwitzer, T.V. Rajan, T. L. Yi, J. N. Ihle, R.J. Matthews, M.L. Thomas, D.R. Beier, Mutations at the Murine Motheaten Locus are Within the Hematopoietic Cell Protein–tyrosine Phosphase (Hcph) Gene, Cell, 1993, pp. 1445–1454.

Georgopoulos, K., M. Bigby, J.H. Wang, A. Molnar, P. Wu, S. windandy, A. Sharpe, "The Ikaros Gene is Required for the Development of all Lymphoid Lineages", Cell, 1994, vol. 79, pp. 143–156.

Wang, B., C. Biron, J. She, K. Higgins, M.J. Sunshine, E. Lacy, N. Lonberg, C. Terhorst, A Block in Both Early T Lymphocyte and Natural Killer Cell Development in Transgenic Mice with High–Copy Numbers of the Human CD3E Gene, Proc. Natl, Acad. Sci., U.S.A., 1994, vol. 91, pp. 9402–9406.

Lowin, B., F. Beermann, A. Schmidt, J. Tschopp, "A Null Mutation in the Perforin Gene Impairs Cytolytic T Lymphocyte– and Natural Killer Cell–Mediated Cytotoxicity", Proc. Natl. Acad. Sci. USA, 1994, vol. 91, pp. 11571–11575.

Takai, T., M. Li, D. Sylvestre, R. Clynes, J.V. Ravetch, "FcR Gamma Chain Deletion Results in Pleiotropic Effector Cell Defects", Cell, 1994, vol. 76, pp. 519–529.

Tak, P.P., J.A. Kummer, C.E. Hack, M.R. Daha, T.J. Smeets, G.W. Erkelens, A.E. meinders, P.M. Kluin, F.C. Breedveld, "Granzyme–Positive Cytotoxic Cells are Specifically Increased in Early Rheumatoid Synovial Tissue", Arthritis Rheum, 1994, vol. 37, pp. 1735–1743.

Kagi, D. et al., "Cytotoxicity Mediated by T Cells and Natural Killer Cells is Greatly Impaired in Perforin–Deficient Mice", Nature, 1994, vol. pp. 31–37.

Walsh, C., et al, "Immune Function in Mice Lacking the Perforin Gene", Proc. Natl. Acad. Sci. USA, 1994, vol. 91, pp. 10854–10858.

Somasundaram, R., et al, "Limitations of the Severe Combined Immunodeficiency (SCID) Mouse Model for Study of Human B–Cell Responses", Scand. J. Immunol., 1995, vol. 41, pp. 384–390.

Ebnet, K., M. Hausmann, F. Lehmann–Grube, A. Mullbacher, M. Kopf, M. Lamers,. M.M. Simon, "Granzyme A–Deficient Mice Retain Potent Cell–Mediated Cytotoxicity", EMBO Journal, 1995, vol. 14, pp. 4230–4239.

Suwa, H., T. Tanaka, F. Kitamura, T. Schiohara, K. Kuida, M. Miyasaka, Dysregulated Expression of the IL–2 Receptor Beta–Chain Abrogates Development of NK Cells and Thy–1+ Dendritic Epidermal Cells in Transgenic Mice, Int. Immunol., 1995, vol. 7, ,pp. 1441–1449.

DiSanto, J.P., W. Muller, D. Guy–Grand, A. Fischer, K. Rajewsky, "Lymphoid Development in Mice with Targeted Deletion of the Interleukin 2 Receptor Gamma Chain", Proc. Natl. Acad. Sci. U.S.A., 1995, vol. 92, pp. 377–381.

Mackarehtschian, K., J.D. Hardin, K.A. Moore, S. Boast, S.P Goff, I.R. Lemischka, Targeted Disruption of the flk/2flt3 Gene Leads to Deficiencies in Primitive Hematopoietic Progenitors, Immunity, 1995, vol. 3, pp. 147–161.

Yokoyama, W., "Natural Killer Cell Receptors Specific for Major Histocompatibility Complex Class 1 Molecules", Proc. Natl. Acad. Sci. USA, Apr. 1995, vol. 92, pp. 3081–3085.

Bendelac, A., O. Lantz, M.E. Quimby, J.W. Yewdell, J.R. Bennink, R.R. Brutkiewicz, "CD1 Recognition by Mouse Nk1+ T Lymphocytes", Science, 1995, vol. 268, pp. 863–865.

Wilder, J.A., C.Y. Koh, D. Yuan, "The Role of NK Cells During In Vivo Antigen–Specific Antibody Responses", J. Immunol., 1996, vol. 156; pp. 146–152.

Barbosa, M.D., Q.A. Nguyen, V.T. Tchernev, J.A. Ashley, J.C. Detter, S.M. Blaydes, S.J. Brandt, D. Chotai, C. Hodgman, R.D. Solari, M. Lovett, S.F. Kingsmore, "Identification of the Homologous Beige and Chediak–Higashi Syndrome Genes", Nature, 1996, vol. 382: pp. 262–265.

Sandhu, J.S., E. Boynton, R. Gorczynski, N. Hozumi, "The Use of Scid Mice in Biotechnology and as a Model for Human Disease", Critical Reviews in Biotechnology, 1996, vol. 16: pp. 95–118.

Murphy, W.J., V. Kumar, M. Bennett, "Rejection of Bone Marrow Allografts by Mice with Severe Combined Immune Deficiency (scid). Evidence that Natural Killer Cells Can Mediate the Specificity of Marrow Graft Rejection", J. Exp. Med., 1996, vol. 165: pp. 1212–1217.

Aguila, H.L., I.L. Weissman, Hematopoietic Stem Cells are not Direct Cytotoxic Targets of Natural Killer Cells, Blood, 1996, vol. 87, pp. 1225–1231.

Kurooka, H. et al, "Rescue of the Hairless Phenotype Innude Mice by Transgenic Insertion of the Wild–Type HfhII Genomic Locus", Int. Immunol., 1996, vol. 8, pp. 961–966.

Lin, Y. Vandeputte, M., Waer, M., "Natural Killer Cell—And macrophage–Mediated Rejection of Concordant Xenografts in the Absence of T and B Cell Responses", J. Immunol., 1997, vol. 158: pp. 5668–5667.

Cui, J.Q., T. Shin, T. Kawano, H. Sato, E. Kondo, I. Toura, Y. Kaneko, H. Koseki, M. Kanno, M. Taniguchi, "Requirement for Val4NKT Cells in IL–12–Mediated Rejection of Tumors", Science, 1997, vol. 278: pp. 1623–1626.

Lieber, M.R., U. Grawunder, X. Wu, M. Yaneva, "Tying Loose Ends: Roles of Ku and DNA–Dependent Protein Kinase in the Repair of Double–Strand Breaks", Current Opinion in Genetics & Development, 1997, vol. 7: pp. 99–104.

Pain–Murrieta, G.D., C.W. Taylor, R.A. Curtis, M.H. Lopez, R.T. Dorr, C.S. Johnson, C.Y. Funk, F. Thompson, E. M. Hersh, "Human Tumor Models in the Severe Combined Immune Deficient (Scid) Mouse", Cancer Chemotherapy & Pharmacology, 1997, vol. 40, pp. 209–214.

Suzuki, H., G.S. Duncan, H. Takimoto, T.W. Mak, "Abnormal Development of Intestinal Lymphocytes and Peripheral Natural Killer Cells in Mice Lacking the IL–2 Receptor Beta Chain", J. Exp. Med., 1997, vol. 185, pp. 499–505.

Zhang, B.N., T. Yamamura, T. Kondo, M. Fujiwara, T. Tabira, "Regulation of Experimental Autoimmune Encephalomyelitis by Natural Killer (NK) Cells", J. Exp. Med., 1997, vol. 186, pp. 1677–1687.

Brown, M. et al, "The Natural Killer Gene Complex: A Genetic Basis for Understanding Natural Killer Cell Function and Innate Immunity", Immunological Reviews, 1997, vol. 155, pp. 53–65.

Yokoyama, W., "The Mother–Child Union: The Case of Missing Self and Protection of the Fetus", Proc. Natl. Acad. Sci. USA, June 1997, vol. 94, pp. 5998–6000.

Petersson, et al, "Allogeneic Heart Transplantation Activates Alloreactive NK Cells", Cell. Immunol., 1997, Vo. 175, pp. 25–32.

Ohteki, T., H. Yoshida, T. Matsuyama, G.S. Duncan, T. W. Mak, P.S. Ohashi, The Transcription Factor Interferon Regulatory Factor1 (IRF–1) is Important During the Maturation of NK1.1+ T Cell Receptor–ab+ (NK1+T) Cells, Natural Killer Cells, and Intestinal Intraepithelial T Cells, J. Exp. Med., 1998, vol. 187, pp. 967–972.

Takeda, K., H. Tsutsui, T. Yoshimoto, O. Adachi, N. Yoshida, T. Kishimoto, H. Okamura, K. Nakanishi, S. Akira, "Defective NK Cell Activity and Th1 Response in IL–18–Deficient Mice", Immunity, 1998, vol. 8, pp. 383–390.

Barton, K., N. Muthusamy, C. Fischer, C.N. Ting, T.L. Walunas, L.L. Lanier, J.M. Leiden, "The Ets–1 Transcription Factor is Required for the Development of Natural Killer Cells in Mice",, Immunity, 1998, vol. 9, pp. 555–563.

Moffat, J.F., L. Zerboni, P.R. Kinghington, C. Grose, H. Kaneshima, A.M. Arvin, "Attenuation of the Vaccine Oka Strain of Varicella–Zoster Virus and Role of Glycoprotein C in Alphaherpesvirus Virulence Demonstrated in the SCID–Hu Mouse", J. Virol, 1998, vol. 72, pp. 965–974.

Yokota, Y., A. Mansouri, S. Mori, S. Sugawara, S. Adachi, S. Nishikawa, P. Gruss, "Development of Peripheral Lymphoid Organs and Natural Killer Cells Depends on the Helix–Loop–Helix Inhibitor Id2", Nature, 1999, vol. 397, pp. 702–706.

Yokoyama, W.M. in press. Chapter. "Natural Killer Cells", Fourth Ed. In Fundamental Immunology, ed. W.E. Paul, New York: Raven.

Smart, Brian A., et al., "The Molecular Basis and Treatment of primary Immunodeficiency Disorders", Current Opinion in Pediatrics, 1997, vol. 9, pp. 570–576.

* cited by examiner

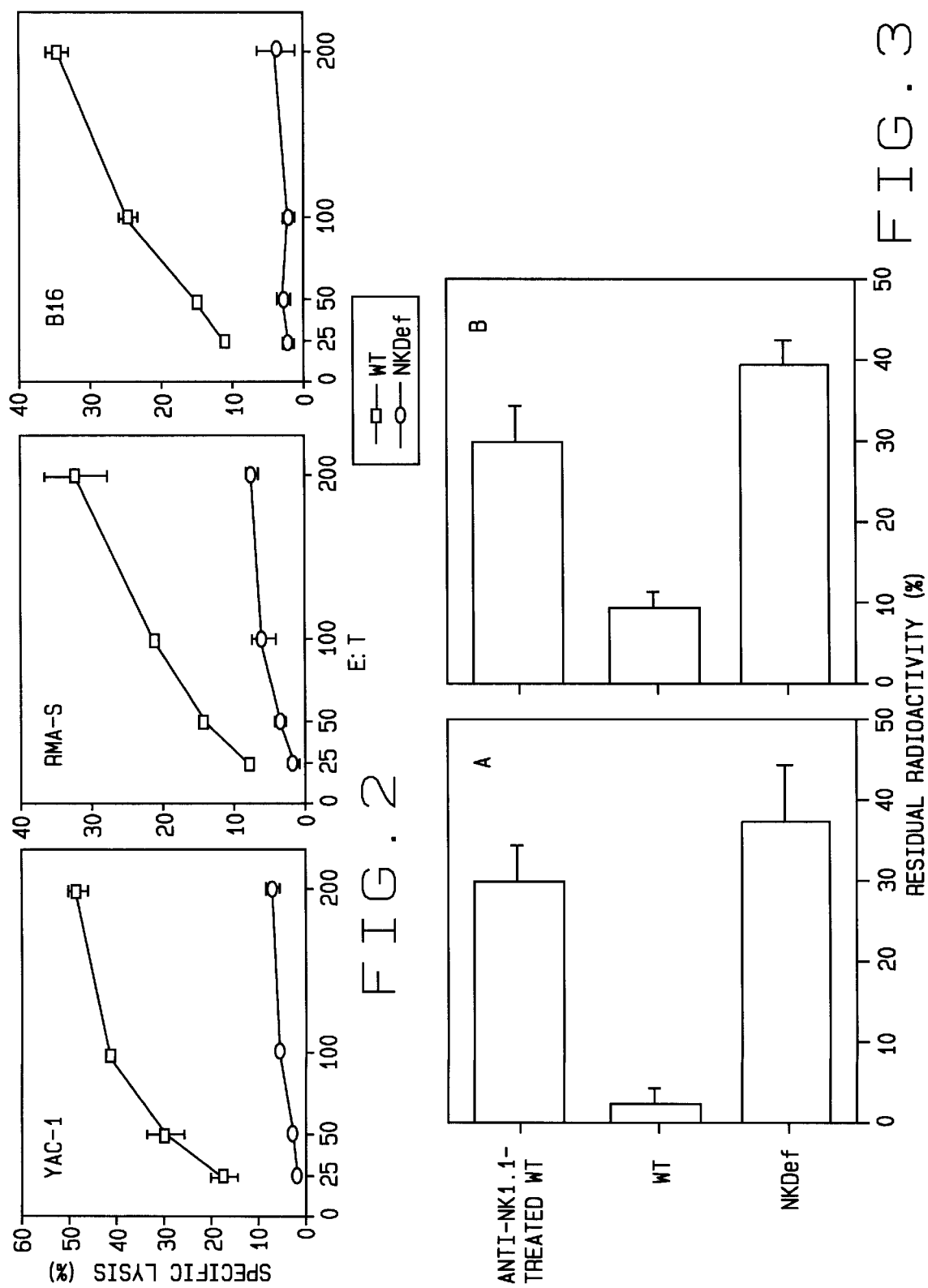

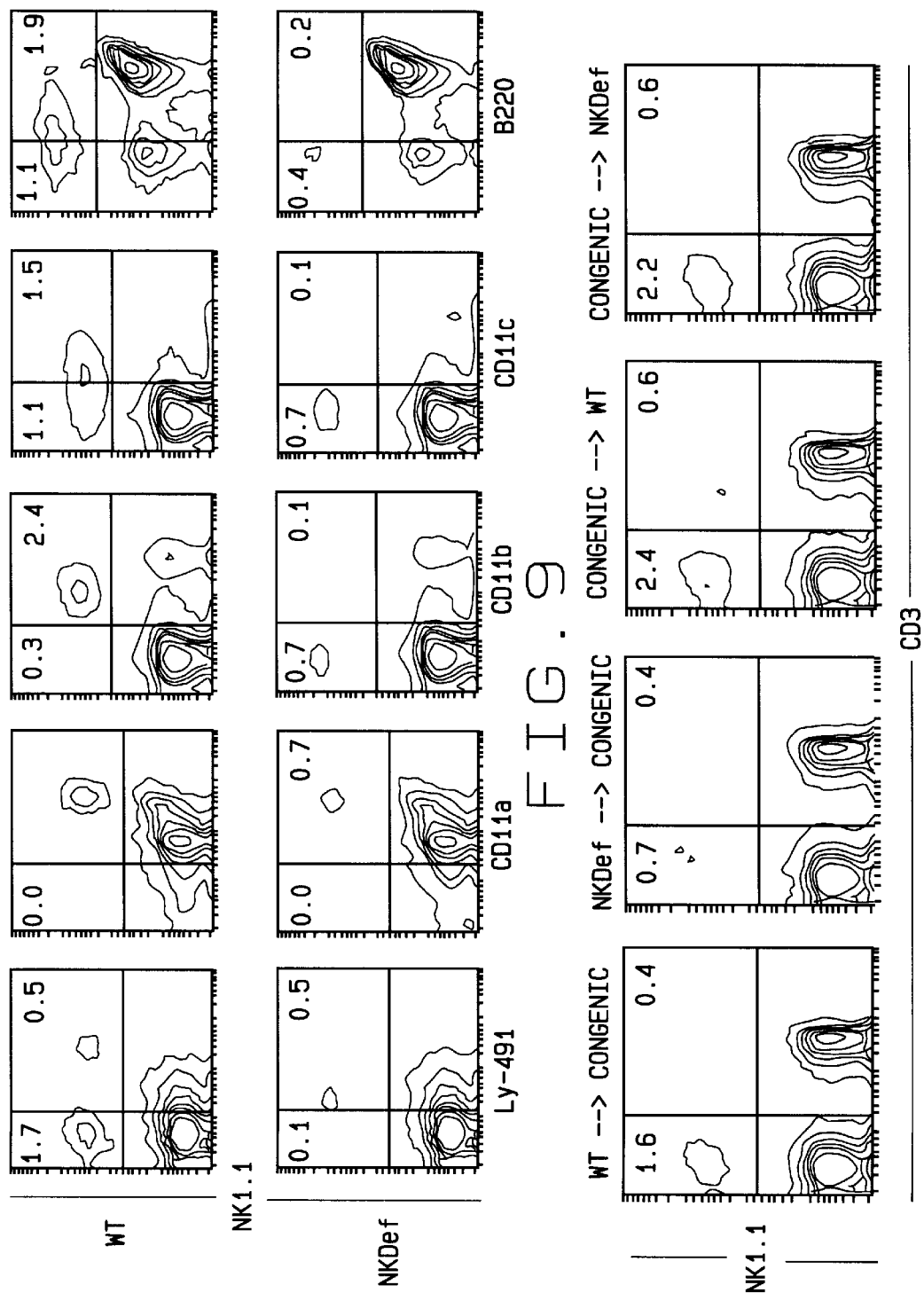

TRANSGENIC MICE DEFICIENT IN NATURAL KILLER CELLS

This application claims the benefit of priority of provisional patent application Ser. No. 60/085,568, filed May 15, 1998, the entire contents of which are herein incorporated by reference.

This invention was made with Government support under National Institutes of Health Grant RO1-AI33903. The Government has certain rights in the invention.

BACKGROUND OF THE INVENTION

The present invention relates to non-human animals which have a natural killer (NK) cell immunodeficiency but have a normal complement of other lymphocytes.

Natural killer (NK) cells were initially described on the basis of their capacity to spontaneously kill certain tumor targets (1). This "natural killing" ability did not require prior deliberate immunization of the host with the tumor cells. This led to the hypothesis that NK cells are involved in tumor surveillance, whereby NK cells eliminate developing cancerous cells before they become established tumors. However, this hypothesis has not been rigorously tested because of the lack of a suitable animal model. Subsequent studies have also suggested that NK cells are involved in other aspects of the immune response. Current data suggest that NK cells have the capacity to respond to certain pathogenic organisms, particularly in the earliest phases (hours to days) of the immune response (2). This contrasts with a more delayed response (days to weeks) in an acquired, specific immune response by B and T cells, that is dependent on clonal expansion and proliferation for specific antibody and cell-mediated responses, respectively (3). On the other hand, NK cells do not appear to require the physical rearrangement of antigen receptor genes, such as such as is required for B (immunoglobulin) and T cell antigen receptors, and are present in mice that lack components of the recombination machinery (4). They must therefore utilize other mechanisms to express a repertoire of receptor molecules that can respond to the universe of tumors or pathogens.

However, NK cells may guide the development of the acquired, specific response, by regulating isotype switching of immunoglobulin isotypes, for example (5). This function appears to be dependent on production of cytokines by the NK cell. Another function attributed to NK cells is their apparent capacity to reject incompatible bone marrow transplants (6). Moreover, NK cells are apparently involved in rejecting solid tissues, such as cardiac allotransplants (7). Thus, NK cells appear to be significant components of the immune system.

All studies of NK cells to date, however, have been limited by the lack of a suitable animal model in which NK cells are selectively and chronically or developmentally absent. The treatment of animals with antibodies which bind to cell surface markers is often employed to deplete cells with those markers in the treated animal. In experiments involving mice, anti-asialoGM1 or anti-NK1.1 antibodies are routinely utilized (8,9). However, those antibodies react with molecules that are expressed on other cells as well as NK cells, such that misleading information can be obtained. For example, a small population of T cells, termed NK/T (or NK1.1+T or NK1 T) cells because they express the NK1.1 antigen otherwise expressed predominantly by NK cells, have been recently shown to be capable of mediating tumor clearance and cytokine production, previously attributed only to NK cells (10). Furthermore, antibody administration is plagued by inherent problems, e.g., that the effect is short lived and that antibody administration may produce other effects on the immune system, such as anti-immunoglobulin formation. Thus, better models for NK cell function in vivo are required.

Immunodeficient hosts can be developed for use as animal models which avoid the problems inherent with the administration of antibodies. Such animals have been used to study various aspects of the immune response. For example, severe combined immunodeficient (scid) mice have a mutation in DNA-dependent protein kinase (DNA-PK) with concomitant abnormalities in the recombination events involved in formation of B and T cell antigen receptors (11). Also, X-linked (xid) mice have a defect in a protein tyrosine kinase which results in a B cell deficiency and nude (nu) mice do not have a thymus and have a defect in T cell development (12). All of these mice have been invaluable in the initial identification and subsequent molecular characterization of B and T cells. As importantly, they have led to an understanding of the contributions of these cells to the normal and deranged immune system. Moreover, these immunodeficient mice have been exploited to carry human cells for the purposes of creating a humanized mouse with which to study infections, tumor formation, drug therapy, and toxicities of various agents (13). On the other hand, these animals have NK cells that can still reject transplanted tissue. Thus, with respect to the elimination of NK cell function, these animals have limitations.

Several mouse strains have been described which contain deficiencies in NK cell function. However, all of these strains also contain other immune deficiencies. These strains have arisen by the mechanisms of spontaneous mutation, gene targeting, or transgene technology.

Spontaneous NK cell deficient mice have been reported but all contain other immune system defects. One of the first described was the beige (Bg) mouse which contains a mutation in a lysosomal transport protein (Lyst) that is not NK cell specific (14). Although this mouse has defects in its capacity to kill tumor targets in vitro, it also has global defects in granule formation, altering the function of other granule-containing lymphocytes. Another mouse, the "motheaten" mouse has a defect in the intracellular tyrosine phosphatase SHP-1 and abnormalities in NK cell development, but also has abnormalities in nearly all hematopoietic lineages (15). Thus, no mouse strain has been reported which has a spontaneous mutation that selectively affects NK cells.

Gene targeting approaches, where the function of a particular gene is eliminated, have resulted in the creation of other mouse strains that have defects in the targeted gene and in NK cells. However, regardless of whether these mice are defective in NK cell function or have a relative absence of NK cells, other aspects of the immune system are invariably and significantly altered due to mutation of the targeted gene (Table 1). Mice with a targeted deficiency in the beta chain of the IL-2 receptor fail to develop NK cells and intestinal epithelial lymphocytes (IEL), and also have defective responses to IL-2 (16). Mice with a targeted deficiency of the common gamma chain of the IL-2 receptor fail to develop T and NK cells (17). Moreover, they are broadly deficient in immune responses because the gamma chain is the signal transduction component of several cytokine receptors, including IL-2, IL-4, IL-7, and IL-15. Mice lacking the Flt-3 molecule have an NK cell deficiency but also have broad defects in hematopoiesis (18). Mice with a targeted deficiency in the Ikaros gene have a defect in lymphopoiesis such that all lymphocytes (B,T, NK cells) fail to develop (19). These mice die in the perinatal period, apparently due to infections. Mice which lack the IRF-1 transcription factor have defects in interferon responses, and hematopoiesis, especially NK, NK/T, and T cell development (20). Moreover, these mice die in the neonatal period. Mice with a targeted deficiency in the Ets-1 transcription factor have an NK deficiency but also have defects in thymic T cell development and T cell antigen receptor-mediated T cell activation (21). Moreover, these mice display an increased perinatal mortality and surviving mice die before adulthood. Mice which lack the Id2 molecule have a defect in NK cell development but still possess some peripheral NK cells with the ability to kill tumor cells (22). Moreover, these mice display an increased neonatal mortality and retarded growth, and fail to develop peripheral lymphoid organs such as lymph nodes and Peyer's patches. Thus, among gene targeted mice, there are no mice with an absence of NK cells with a relative sparing of other lymphocyte lineages and with an otherwise intact immune system.

TABLE 1

NK CELL DEFICIENCY IN TARGETED MUTANT OR TRANSGENIC MICE

| TARGETED GENE OR TRANSGENE (Tg) | DEFECTS | REFERENCE |
| --- | --- | --- |
| βchain of IL-2R | NK, IEL development | (16) |
| γchain of IL-2R | T, NK cell development | (17) |
| Flt-3 | Hematopoiesis | (18) |
| Ikaros | Lymphopoiesis (B, T, NK) | (19) |
| IRF-1 | Abnormal interferon responses, defective hematopoiesis, NK, NK/T, T cell development | (20) |
| Perforin | Killing by CTLS and NK cells | (26) |
| Granzyme | Killing by CTLs and NK cells | (27) |
| FcγRIII | ADCC by NK cells, macrophage | (28) |
| IL-18 | IL-18 | (29) |
| Tgε26 (Hu CD3ε) (Tg) | T, NK cell development | (23) |
| βchain of IL-2R (Tg) | NK, epidermal T cells | (24) |
| Granzyme-Diptheria toxin (Tg) | NK, CD8 + T cells | (25) |
| Ets-1 | NK cell development and T cell activation | (21) |
| Id2 | Development of peripheral lymphoid organs and NK cells | (22) |

Several strains of transgenic mice have been developed which lack NK cells. The Tgε26 mouse contains high copy numbers of the human CD3ε gene (23). Although it lacks NK cells, it also lacks T cells. An IL-2 receptor β chain transgenic mouse lacks NK cells but also lacks epidermal T cells (24). In addition, T cells in those transgenic mice are hyper-responsive to IL-2. The granzyme A-diptheria toxin mouse lacks a substantial number of NK cells but is also devoid of T cell populations (25). Thus, no transgenic mice with a selective deficiency of NK cells has been reported.

Another strategy to create an NK cell deficient mouse is to generate mice with abnormalities in NK cell effector mechanisms such that the NK cells are present but functionally impotent. Perforin-deficient and granzyme-deficient mice contain NK cells, but these NK cells have deficiencies because perforin and granzymes are normally contained in NK cell granules that are released upon activation to mediate killing of cellular targets (26,27). However, because these components are also required for the cytolytic activity of cytotoxic T lymphocytes (CTL), the CTLs are also defective. Mice with defects in the FcγRIII molecule contain NK cells but fail to develop antibody-dependent cellular cytotoxicity (ADCC) because this molecule is utilized by the NK cell for this response (28). However, natural killing is intact and other cells that normally express this receptor also fail to generate ADCC function. IL-18 defective mice have abnormal NK cell responses although the number of NK cells is apparently normal (29). Thus, mice with defects in NK cell effector function also have other defects. On the other hand, NK cells present in these mice presumably possess normal NK cell effector functions such as interferon-γ production, other than those disrupted effector functions.

Therefore, no animal species has been reported which has either an absolute or functional deficiency in NK cells with relative sparing of other immune system components. The development of such an animal, such as the mouse disclosed herein, represents a significant advance for the scientific fields of immunology, cancer, hematology, transplantation, and infectious diseases.

With regard to xenogeneic transplantation, host immune systems are involved in rejecting transplanted tissues. Thus far, it has been possible to transplant many human tissues into animals that lack B and T cells. This has obvious utility in that the animals can then be infected with pathogens that infect the implanted human tissues or human tumors, permitting testing of new therapies or virulence factors (30, 31). However, not every human tissue can apparently be transplanted into the B and T cell deficient animals, perhaps reflecting the capacity of NK cells to reject transplants (13). Moreover, injection of antibodies that react with NK cells result in enhanced xenogeneic transplant survival, implying a role for NK cells in transplant rejection. The development of animal models that lack B, T, and NK cells, yet which are viable, reproductive animals that reach adulthood will be useful in further investigation.

SUMMARY OF THE INVENTION

Among the several objects of the invention, therefore, may be noted the provision of a transgenic mammal in which there is a substantial deficiency of NK cells with normal immunoglobulin levels and normal numbers of T and B lymphocytes in peripheral blood and spleen. Also provided are transgenic mammals with combined deficiencies in NK along with T and/or B cells, produced by mating the NK deficient transgenic mammal with mammals deficient in T and/or B cells. These mammals are useful for studying the immunological role of NK, T, and B cells and as animal models for human diseases such as immunodeficiency diseases or cancer.

A further object of the invention is the provision of non-human mammals which do not reject or have a substantially diminished capacity to reject transplants of human tissues. Such mammals are useful for assessing, for example, the toxicity, carcinogenicity, or therapeutic effect of chemical compositions on the transplanted human tissue. They can also help identify disease agents.

Another object of the invention is the provision of non-human mammals with substantially diminished ability to kill or reject cancer tumors. These mammals are useful for studying cancer and for developing cancer therapies. They should also have increased susceptibility to carcinogenic factors and are thus useful to assess the carcinogenic potential of administered agents.

Therefore, the present invention is directed to a non-human mammal genetically having:
 a) a deficiency of natural killer activity of at least 50% as measured by reduction in specific lysis of YAC-1, RMA-S. or B16 tumor cells; and
 b) a substantially normal complement of other lymphocytes.

The present invention is further directed to a non-human mammal which comprises a transgene which has a granzyme A gene wherein a Ly49A gene is inserted into the granzyme A gene such that the Ly49A gene is expressed.

The invention is also directed to a method of producing a transgenic non-human mammal which has a deficiency in natural killer activity of at least 50% as measured by reduction in specific lysis of YAC-1, RMA-S, or B16 tumor cells. The method comprises the following steps:
 a) introducing a transgene into an embryonal cell of the mammal, the transgene comprising a granzyme A gene wherein a Ly49A gene is inserted into the granzyme A gene such that the Ly49A gene is expressed; and
 b) identifying a mammal derived from the embryonal cell which contains the stably integrated transgene and has a deficiency of natural killer cells.

The invention is also directed to a non-human mammal which comprises i) a granzyme A gene wherein a Ly49A gene is inserted into the granzyme A gene such that the Ly49A gene is expressed, and ii) a substantial deficiency in T cells.

The present invention is further directed to a method of producing a progeny non-human mammal which has: i) a deficiency of natural killer activity of at least 50% as measured by reduction in specific lysis of YAC-1, RMA-S, or B16 tumor cells, and ii) a substantial deficiency in T cells. The method comprises the following steps:
 a) mating a first non-human mammal with a second non-human mammal, wherein the first non-human mammal has the deficiency of natural killer activity and a substantially normal complement of other lymphocytes, and wherein the second non-human mammal has a substantial deficiency in T cells and a substantially normal complement of other lymphocytes; and
 b) selecting progeny derived from the mating of step a) which has a deficiency of natural killer cells and T cells.

The present invention is also directed to a non-human mammal produced by the method of described immediately above.

The invention is further directed to a non-human mammal which comprises i) a deficiency of natural killer activity of at least 50% as measured by reduction in specific lysis of YAC-1, RMA-S, or B16 tumor cells, and ii) a substantial deficiency in B cells.

The invention is also directed to a non-human mammal which comprises i) a granzyme A gene wherein a Ly49A gene is inserted into the granzyme A gene such that the Ly49A gene is expressed, and ii) a substantial deficiency in B cells.

The invention is still further directed to a method of producing a progeny non-human mammal which has i) a deficiency of natural killer activity of at least 50% as measured by reduction in specific lysis of YAC-1, RMA-S, or B16 tumor cells, and ii) a substantial deficiency in B cells. The method comprises the following steps:
 a) mating a first non-human mammal with a second non-human mammal, wherein the first non-human mammal has the deficiency of natural killer activity and a substantially normal complement of other lymphocytes, and wherein the second non-human mammal has a substantial deficiency in B cells and a substantially normal complement of other lymphocytes; and
 b) selecting progeny derived from the mating of step a) which has a deficiency of natural killer cells and B cells.

The present invention is also directed to a non-human mammal produced by the method described immediately above.

The present invention is further directed to a non-human adult mammal which comprises i) a deficiency of natural killer activity of at least 50% as measured by reduction in specific lysis of YAC-1, RMA-S, or B16 tumor cells, ii) a deficiency of T cells, and iii) a deficiency of B cells.

The present invention is still further directed to a non-human mammal which comprises i) a granzyme A gene wherein a Ly49A gene is inserted into the granzyme A gene such that the Ly49A gene is expressed, ii) a substantial deficiency in T cells, and iii) a substantial deficiency in B cells.

The invention is also directed to a method of producing a progeny non-human mammal which has i) a deficiency of natural killer activity of at least 50% as measured by reduction in specific lysis of YAC-1, RMA-S, or B16 tumor cells, ii) a deficiency of T cells, and iii) a deficiency of B cells. The method comprises the following steps:
 a) mating a first non-human mammal with a second non-human mammal, wherein the first non-human mammal has the deficiency of natural killer activity and a substantially normal complement of other lymphocytes, and wherein the second non-human mammal has a substantial deficiency in T cells and B cells; and
 b) selecting progeny derived from the mating of step a) which are deficient in natural killer cells, T cells, and B cells.

The present invention is also directed to a non-human mammal produced by the method described immediately above.

The invention is further directed to a method of producing a non-human mammal which has i) a deficiency of natural killer activity of at least 50% as measured by reduction in specific lysis of YAC-1, RMA-S, or B16 tumor cells, ii) a deficiency of T cells, and iii) a deficiency of B cells. The method comprises the following steps:
 a) directing a first mating of a first non-human mammal with a second non-human mammal, then directing a second mating of the progeny derived from the first mating with a third non-human mammal, wherein one of the non-human mammals has the deficiency of natural killer activity and a substantially normal complement of other lymphocytes, wherein another of the non-human mammals has a substantial deficiency in T cells and a substantially normal complement of other lymphocytes, and wherein the remaining nonhuman mammal has a substantial deficiency in B cells and a substantially normal complement of other lymphocytes; and
 b) selecting progeny derived from the second mating which has a deficiency in natural killer cells, T cells and B cells.

The present invention is also directed to a non-human mammal produced by the method described immediately above.

In a further embodiment, the present invention is directed to a method for producing an animal containing human tissues. The method comprises the following steps:

a) providing a non-human mammal which has a deficiency of natural killer activity of at least 50% as measured by reduction in specific lysis of YAC-1, RMA-S, or B16 tumor cells, wherein the non-human mammal comprises a transgene comprising a mouse granzyme A gene wherein a Ly49A gene is inserted into the granzyme A gene such that the Ly49A gene is expressed; and b) transplanting human tissue into the non-human mammal.

The invention is further directed to a method for evaluating the effects of a composition on human tissue. The method comprises the following steps:

a) providing a non-human mammal which has a deficiency of natural killer activity of at least 50% as measured by reduction in specific lysis of YAC-1, RMA-S, or B16 tumor cells, wherein the non-human mammal comprises a transgene comprising a mouse granzyme A gene wherein a Ly49A gene is inserted into the granzyme A gene such that the Ly49A gene is expressed; and b) contacting the composition with the human tissue in the animal.

Additionally, the present invention is directed to a method for determining whether a human disease is caused by a pathogenic agent. The method comprises the following steps:

a) providing a non-human mammal which has a deficiency of natural killer activity of at least 50% as measured by reduction in specific lysis of YAC-1, RMA-S, or B16 tumor cells, wherein the non-human mammal comprises a transgene comprising a mouse granzyme A gene wherein a mouse Ly49A gene replaces the start codon of the mouse granzyme A gene;

b) transplanting non-diseased human tissue into the non-human mammal;

c) contacting diseased human tissue with the non-diseased human tissue;

d) determining whether the non-diseased human tissue acquires the disease.

In an additional embodiment, the invention is directed to a method of studying natural killer cells. The method comprises the following steps:

a) obtaining a NKDef mouse and a mouse having wild-type natural killer activity;

b) infecting the NKDef mouse and the mouse having wild-type natural killer activity with a pathogen or with cancer cells; and c) evaluating differences in immunity between the NKDef mouse and the mouse having wild-type natural killer activity.

The present invention is also directed to mouse natural killer cells having a deficiency of interferon-γ production of at least 50% when compared to wild-type mouse natural killer cells.

The present invention is additionally directed to a method of studying natural killer cells. The method comprises comparing natural killer cells from an NKDef mouse with natural killer cells from a mouse having wild-type natural killer activity.

Other features, objects and advantages of the present invention will be in part apparent to those skilled in the art and in part pointed out hereinafter. All references cited in the instant specification are incorporated by reference. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIG. 2 is three graphs which summarize experimental results demonstrating that splenocytes from NKDef mice manifest impaired in vitro natural killing. C57BL/6 (wild type, WT) and heterozygous NKDef mice were injected intraperitoneally with 150 μg of poly-I:C. 24 hr later, the spleen cells were used in 4 hr $^{51}$Cr-release cytotoxicity assays against YAC-1 (lymphoma), RMA-S (T cell lymphoma) and B16 (melanoma) target cells at varying effector:target (E:T) ratios as indicated. Results are expressed as the mean percent-specific lysis+SD of triplicate wells.

FIG. 3 is two graphs which demonstrate the impaired acute in vivo rejection of tumor cells in NKDef mice. Anti-NK1.1-depleted mice, WT and heterozygous NKDef mice were injected intravenously with $^{121}$I-UdR-labeled $3 \times 10^5$ YAC-1 (panel A) and $1 \times 10^5$ B16 (panel B) cells. The residual radioactivity in the lungs was determined after 4 hr and 8 hr, respectively. Where indicated, WT mice were injected intraperitoneally (i.p.) with 200 μg of anti-NK1.1 monoclonal antibody (mAb) 2 days before tumor inoculation. Results are expressed as the mean percent residual radioactivity±SD from 3–5 mice per group.

FIG. 9 is graphs representing flow cytometry results which show the abnormal cell surface phenotype of NK1.1$^+$ CD3$^-$ cells in NKDef mice. Viable spleen cells were separated using Lympholyte-M and subjected to triple staining with Cy-conjugated anti-CD3, PE-conjugated and FITC-conjugated antibody specific for the indicated marker. Shown are profiles for marker expression generated on cells gated on CD3-negative cell population in WT and NKDef mice. The numbers represent the percentage of cells within the quadrant among all viable cells.

FIGS. 10(A–B) are graphs which demonstrate the intrinsic block in NK cell development in NKDef mice. Bone marrow cells from WT or NKDef mice were transferred into irradiated C57BL/6-Ly5 congenic mice or vice versa as indicated. FIG. 10A shows a flow cytometry analysis of chimeric mice. Profiles for the expression of NK1.1 and CD3 on spleen cells are shown.

DETAILED DESCRIPTION OF THE INVENTION

The term "transgenic" refers to an organism which contains stably inherited genetic material which was inserted into the organism or its ancestors by molecular genetic manipulation. A "transgene" refers to the genetic material which was inserted.

The term "genetically" refers to a trait which is conferred by the translation of genetic material in an animal.

The term "wild-type" refers to a natural or unmutated organism or characteristic.

When referring to matings of non-human animals, the term "progeny derived from the mating" may include the progeny of matings, including backcrosses, made with progeny derived from the original mating.

The procedures disclosed herein which involve the molecular manipulation of nucleic acids are known to those skilled in the art. See generally Joseph Sambrook et al. (1989), "Molecular Cloning, A Laboratory Manual", second ed., Cold Spring Harbor Laboratory Press.

Generation of NKDef Non-human Mammals

The present invention provides non-human mammals which are substantially deficient in NK cells, but which have a substantially normal complement of other lymphocytes. Present in these mice are B cells and a profile of T cell types which resembles that found in wild-type animals. A substantially normal major histocompatibility complex is present, as are other common cell surface markers. This phenotype is designated NKDef. Such NKDef mammals are generated by transforming the mammals with a transgene comprising a Ly49A cDNA inserted into a granzyme A gene such that the promoter activity of the granzyme A gene is intact, but the granzyme A structural gene cannot be translated. Since NK cell activity and structure is very similar among mammals, any non-human mammal which is amenable to transformation technology is a suitable subject for this procedure.

Figure 1:
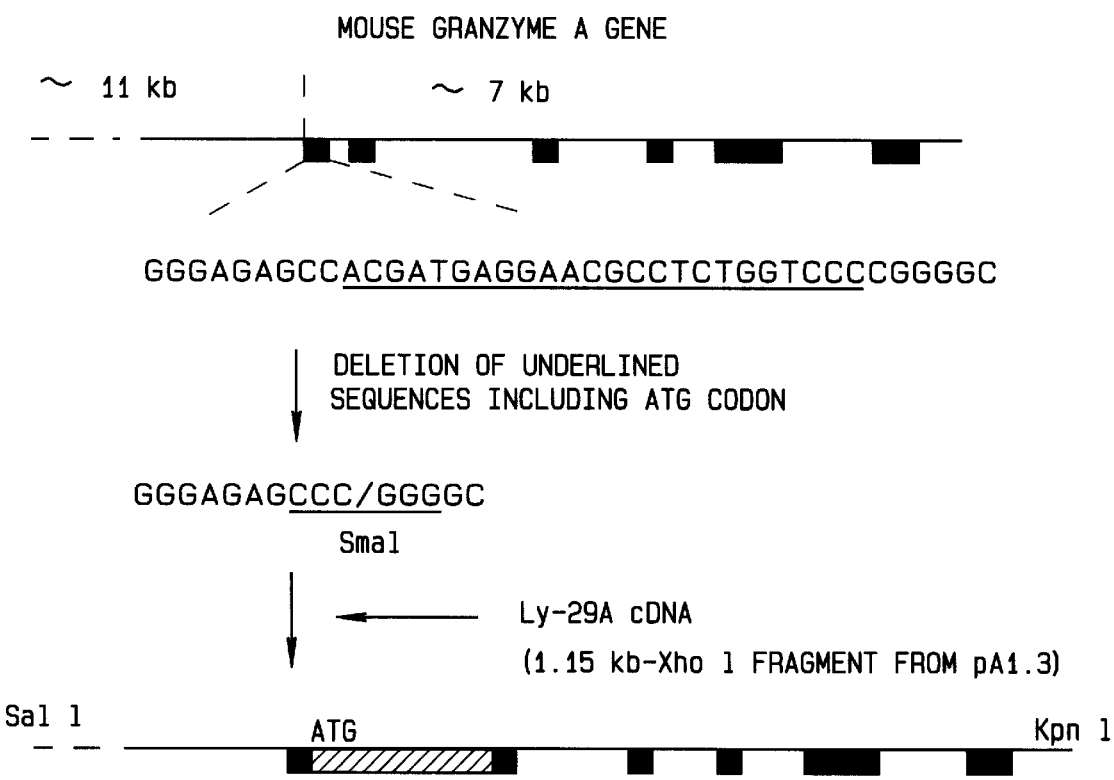
FIG. 1 is a graphic depiction of the molecular construct used to generate the NKDef Ly-49A transgenic mice of the present invention. A partial map of the murine granzyme A gene is shown at the top; exons are displayed as filled boxes and the hatched rectangle represents the Ly49A CDNA. After removal of the granzyme A translational initiation codon, the Ly-49A CDNA was inserted into exon 1 of the murine granzyme A gene. The 19 kb SalI-KpnI fragment was purified and micro-injected into fertilized eggs of C57BL/6 mice by standard techniques to create transgenic (NKDef) mice.

In the preferred embodiment, the start codon of the mouse granzyme A gene (25) is replaced with the mouse Ly49A gene (32). To create this gene construct, the start codon of the mouse granzyme A gene is preferably deleted by standard molecular biology techniques, then replaced with a SmaI restriction enzyme recognition site (FIG. 1). The Ly49A cDNA representing a 1.15 kb XhoI fragment of the pA1.3 plasmid (32) is then cloned into the SmaI site. Other genes may also be incorporated into the transgene construct, for example coat color genes or other marker or selectable genes known in the art, to facilitate identification or selection of transgenic animals.

The granzyme A/Ly49A construct is then used to transform a non-human mammal, preferably a murine, more preferably a mouse, by any method known in the art. See, e.g. Reference 33. In the preferred embodiment, the construct is excised from the backbone of the preferred plasmid (FIG. 1) with SalI and KpnI restriction enzyme digestion and is injected into the pronucleus of fertilized mouse C57BL/6 eggs by standard techniques (33). Pups are then derived, weaned, and tagged. At the time of weaning, tails are preferably harvested for examination of DNA. To determine the expression of the Ly49A marker in the lymphocytes of putative transgenic animals, a novel method is preferred. In this method, blood, preferably less than about 100 $\mu$l, from the tail excision is combined with cell culture medium containing sufficient interleukin-2 (IL-2) to activate NK and some T cells. Preferably, the blood is placed into a well of a 96 well microtiter culture plate and combined with RPMI 1640 media containing 10% fetal calf serum and recombinant human IL-2 (1000 U/ml). The blood-media-IL-2 combination is incubated, preferably about 10 days, to allow the lymphocytes to multiply. The Ly49A markers and other lymphocyte markers are then preferably analyzed by flow cytometry. This assay can also be used to analyze immune cell surface marker profiles of any animal, where any growth factor or combination of growth factors may be used in place of IL-2. Mice which have the NKDef phenotype and carry the transgene express Ly49A on nearly all IL-2-activated cells. The NKDef phenotype may also be identified before in vitro IL-2 expansion by flow cytometry using anti-NK1.1 antibodies, since there are markedly less cells expressing NK1.1 in the blood of NKDef animals than in wild type animals (see FIG. 8). The identification of NKDef animals is preferably confirmed by Southern blot or PCR analysis of tail DNA using the Ly49A gene as a probe or transgene specific primers.

NKDef mice are phenotypically normal and fertile. Also, NKDef mice do not show any abnormality in the development of all of the lymphoid organs inspected (spleen, thymus, bone marrow, lymph nodes, and Peyer's patches).

The mice expressing the NKDef phenotype are heterozygous. The homozygous condition for the genotype which confers the NKDef phenotype appears to be lethal, since a mating of two mice expressing the NKDef phenotype does not "breed true", i.e., none of the progeny of that mating will, when mated with another mouse, produce progeny all of which have the NKDef phenotype. The NKDef:wild-type ratios of progeny from a NKDef X NKDef mating are also consistent with the premise that the NKDef genotype is lethal when homozygous.

Characterization of the NKDef Mouse

Figure 5:
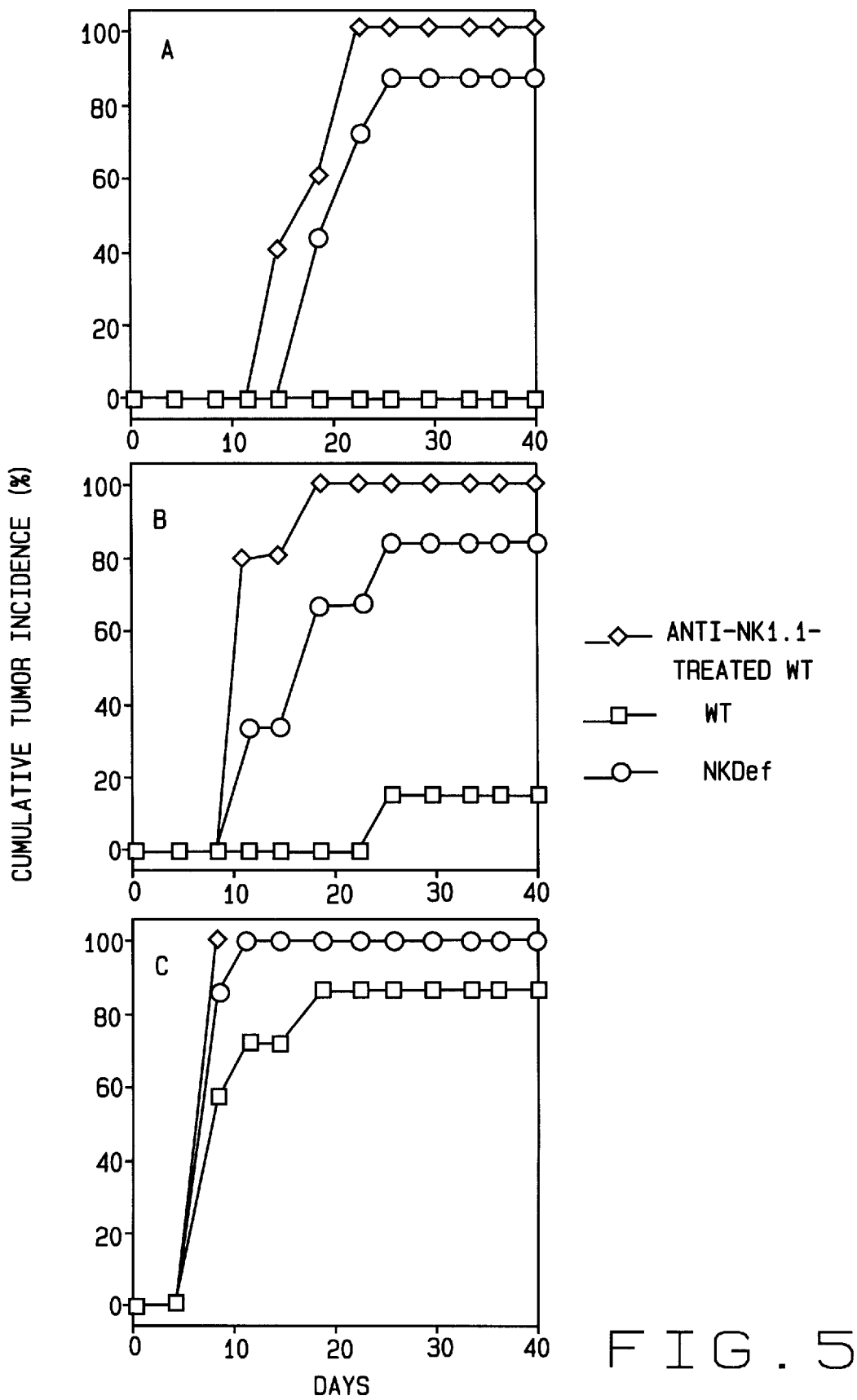
FIGS. 5(A–C) are three graphs which show the long-term growth of RMA-S tumor cells in vivo. $10^2$ (A), $10^3$ (B), or $10^5$ (C) RMA-S cells were injected subcutaneously into the flanks of anti-NK1.1-treated mice (3–5 mice per group), WT (7 mice per group) and heterozygous NKDef (6–7 mice per group), respectively. Mice were monitored for palpable tumors twice weekly. Anti-NK1.1-treated WT mice received 200 μg of anti-NK1.1 mAb i.p. on days −4, −2, +7, +14 and +21 where indicated.
Figure 4:
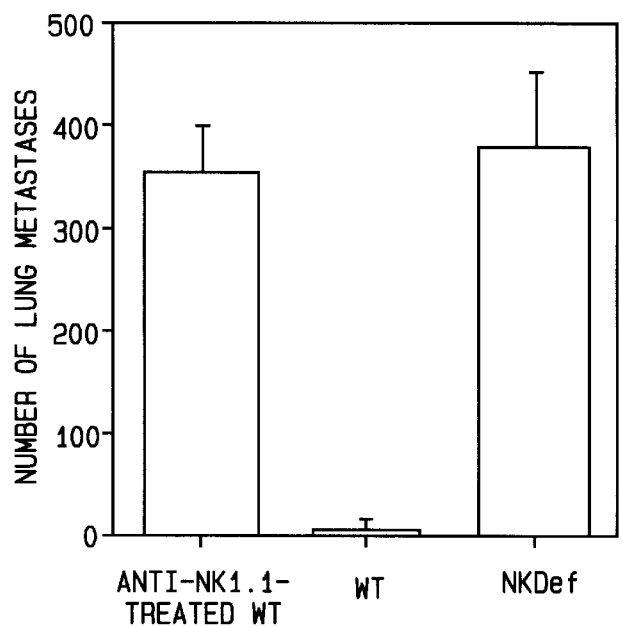
FIG. 4 is a graph which shows the increased formation of experimental lung metastases in NKDef mice. Mice were injected intravenously with $3 \times 10^4$ B16 cells on day 0. The number of macroscopic tumor metastases in the lung was counted on day 14. Anti-NK1.1-treated WT mice received 200 μg of anti-NK1.1 i.p. on days −2, +2 and +7. Results are represented as the mean number±SD from 4 mice per group.

Heterozygous transgenic (NKDef) mice fail to demonstrate the wild-type NK functional activity by several criteria. First, spleen cells from NKDef mice do not display natural killing in vitro. After poly-I:C treatment, splenocytes from NKDef mice have undetectable in vitro cytotoxic activity in 4 hr $^{51}$Cr-release assays against YAC-1 tumor cells (FIG. 2), a cellular target that is widely accepted as being sensitive to natural killing (34). Moreover, the NKDef spleen cells fail to kill RMA-S and B16 tumor targets. In contrast, normal mice, including non-transgenic littermates, display easily detectable splenocyte killing of YAC-1, RMA-S, and B16 after poly-I:C treatment. Second, NK cells are thought to be involved in the acute rejection of tumor cells in vivo. This can be measured by the in vivo capacity to clear targets from the lungs within 4 hrs after administration of radiolabeled tumor by intravenous infusion via the tail vein (35). In normal mice, NK cells appear to eliminate tumor accumulation in the lung as evidenced by low radioactivity in the lungs whereas anti-NK1.1 treatment 2 days prior to tumor injection results in marked increase in radioactivity in the lung (FIG. 3). By contrast, the NKDef mice accumulate radioactivity in the lung even when untreated. This is recapitulated in a longer term experiment (14 days) demonstrating that intravenously administered melanoma cells produce macroscopic (black) tumor foci in the lungs of NKDef mice and normal mice pretreated with anti-NK1.1 whereas no tumor foci develop in normal mice (FIG. 4). Third, in longer-term assays, the NKDef mice cannot reject MHC class I-deficient tumor cells transplanted subcutaneously whereas normal mice eliminate the tumor as determined by absence of tumor growth in serial observations over a 40 day interval (FIG. 5). At cell doses that fail to generate palpable tumors in WT mice, the NKDef mice accumulate tumors, similar to anti-NK1.1-treated WT mice. Thus, the NKDef mice fail to demonstrate anti-tumor activity in vitro and in short, intermediate, and long term in vivo assays.

Figure 6:
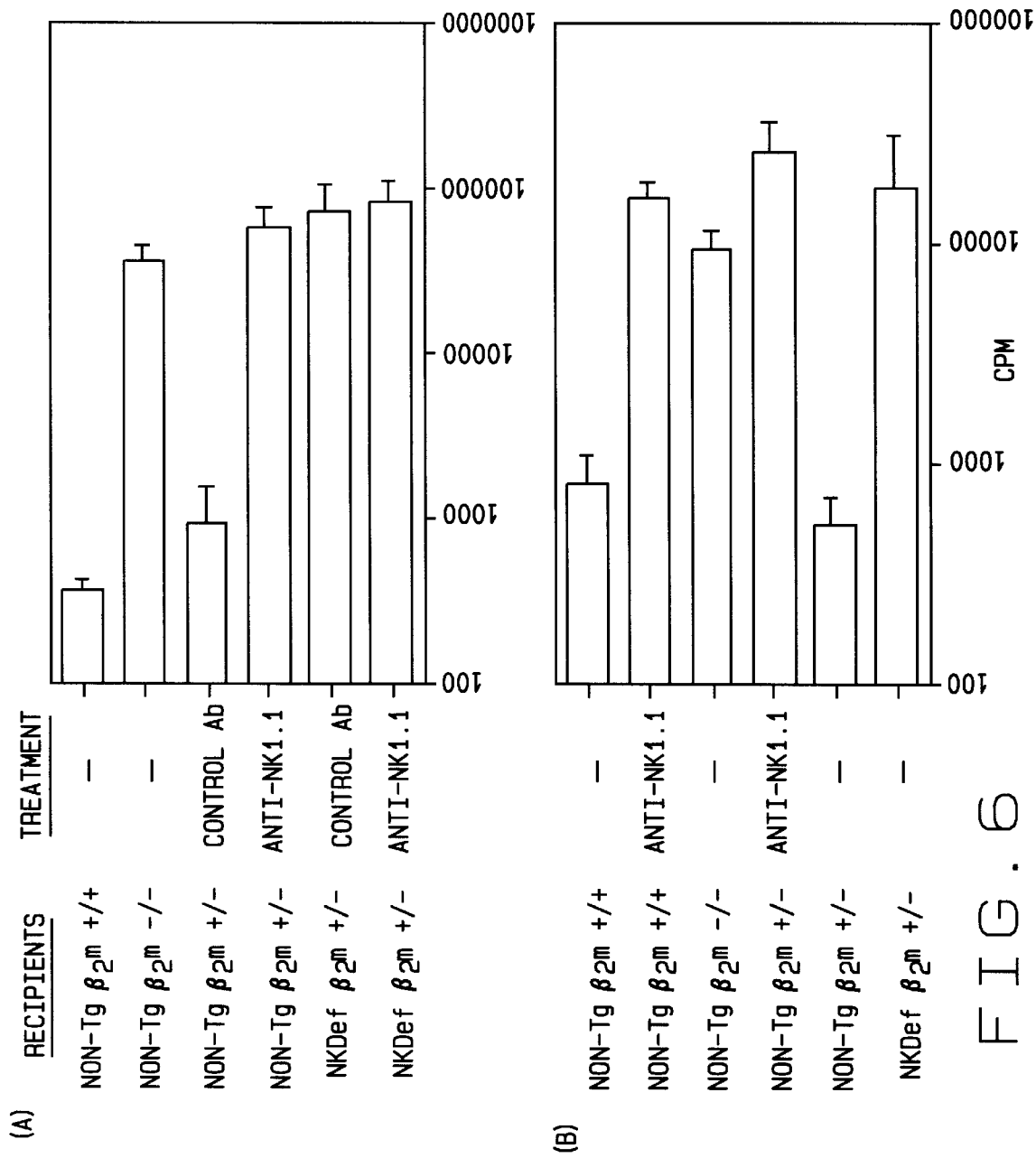
FIGS. 6(A–B) are two graphs which demonstrate the impaired rejection of transplanted bone marrow in NKDef mice. Anti-NK1.1-treated mice were injected intraperitoneally with 200 μg of anti-NK1.1 or control antibody on day −2 where indicated. After 9.5 Gy irradiation on day 0, β2m-deficient (β2m$^{−/−}$), β2m-sufficient (β2m$^{+/−}$) , non-transgenic (non-NKDef) or heterozygous transgenic (NKDef) mice were transplanted with $5 \times 10^5$ (A) or $5 \times 10^6$ (B) of bone marrow cells from C57BL/6–β2m$^{-/-}$ mice via tail vein injection. On day 5, the mice were injected intravenously with 3 μCi $^{125}$I-UdR and $1 \times 10^{-11}$M Fudr. On day 6, the spleens were removed and counted in a γ-counter with radiolabel incorporation as an index of hematopoietic precursor cell proliferation.

NK cells are also thought to be involved in bone marrow transplant rejection, particularly when the donor cells are derived from mice deficient in MHC class I, such as $\beta$2-microglobulin-deficient ($\beta$2m$^{-/-}$) mice, and transferred to irradiated hosts (36). This is determined by injecting $^{125}$I-UdR 5 days after transplantation and measuring the degree of radioisotope incorporation in the spleen of the transplanted mice on day 6. Irradiated WT mice fail to incorporate radiolabel in the spleen after transplantation of $\beta$2m$^{-/-}$ bone marrow, indicating rejection. By contrast, the NKDef mice fail to reject $\beta$2m$^{-/-}$ bone marrow, permitting $^{125}$I-UdR incorporation (FIG. 6). This is similar to anti-NK1.1 treated normal mice or syngeneic $\beta$2m$^{-/-}$ hosts that also fail to reject $\beta$2m$^{-/-}$ bone marrow. Thus, the NKDef mice fail to demonstrate functions associated with NK cells, including in vitro natural killing of tumors, in vivo rejection of tumors, and in vivo rejection of $\beta$2m$^{-/-}$ bone marrow.

Figure 8:
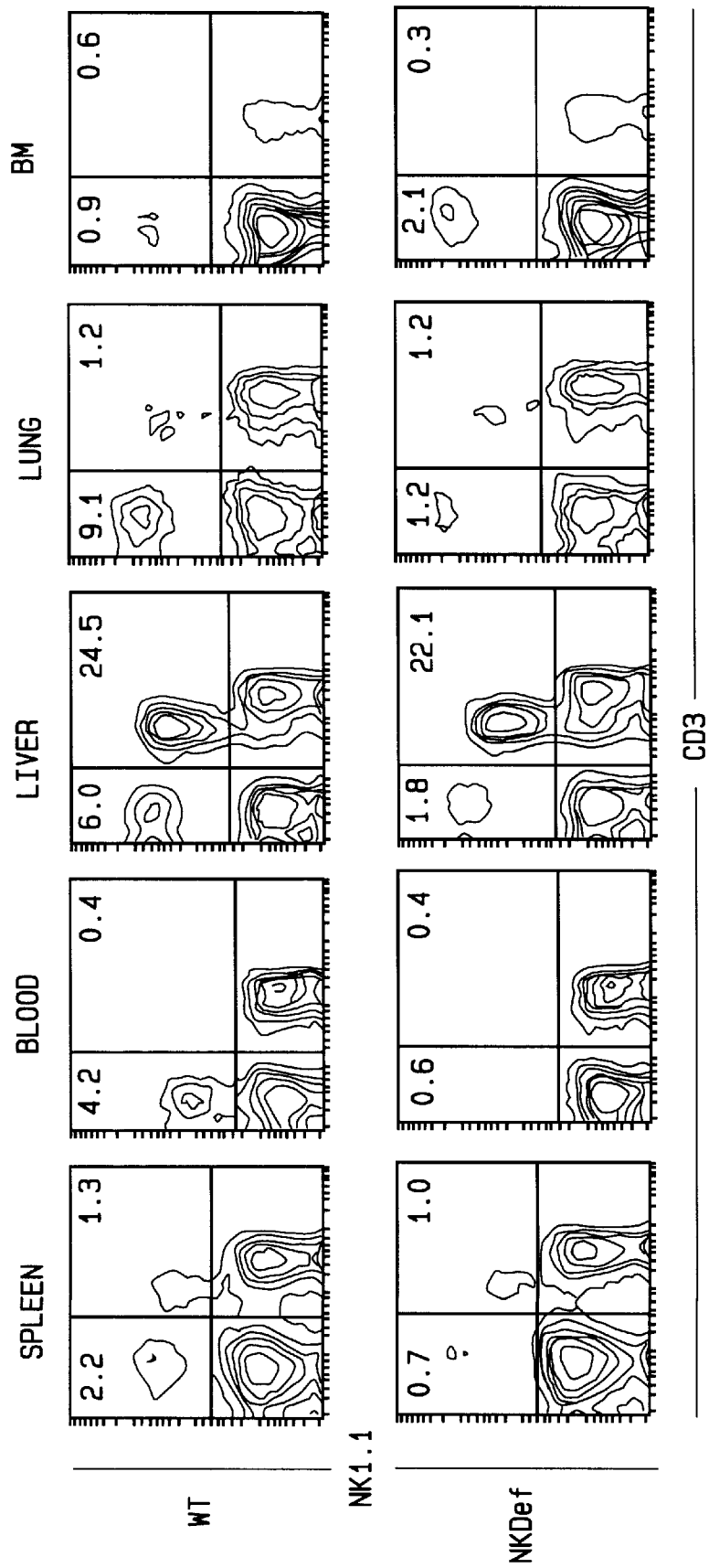
FIG. 8 is graphs representing flow cytometry results which demonstrate the marked decrease of peripheral NK1.1$^+$CD3$^-$ cells in NKDef mice. Single cell suspensions were prepared from indicated organs and subjected to dual staining with PE-conjugated anti-NK1.1 and FITC-conjugated anti-CD3 antibodies. The numbers represent the percentage of cells within the quadrant among all viable cells.

The other lymphocyte constituents of NKDef mice are apparently normal. There are normal numbers of cells in the various lymphoid organs such as the spleen, peripheral blood, and thymus. There are also normal numbers of T cells and T cell subsets as determined by expression of CD3$\epsilon$, CD4, and CD8 in flow cytometric examination. Furthermore, there are normal numbers of B cells as determined by surface immunoglobulin expression. Functional activities of T and B cells appear to be normal. The NKDef mice are still capable of rejecting skin grafts, a function attributable to T cells. Immunoglobulin levels are normal and in vitro mitogen responses by the NKDef B and T cells are normal (data not shown). Finally, the NK/T cell number is apparently normal, with levels at least 80% of normal numbers in spleen, peripheral blood, liver, lung, and bone marrow (FIG. 8). Moreover, functional activities attributed to NK/T cells, such as IL-4 production after anti-CD3 administration are essentially normal (data not shown). Thus, NKDef mice appear to have normal T and B cells and normal NK/T cells, but have a deficiency of natural killer activity of greater than 80%.

The functional NK cell deficiency can be restored by transfer of spleen cells from scid mice which have deficiencies in normal, mature B and T cells, including NK/T cells (37). The scid mice have functionally normal NK cells (4).

Figure 7:
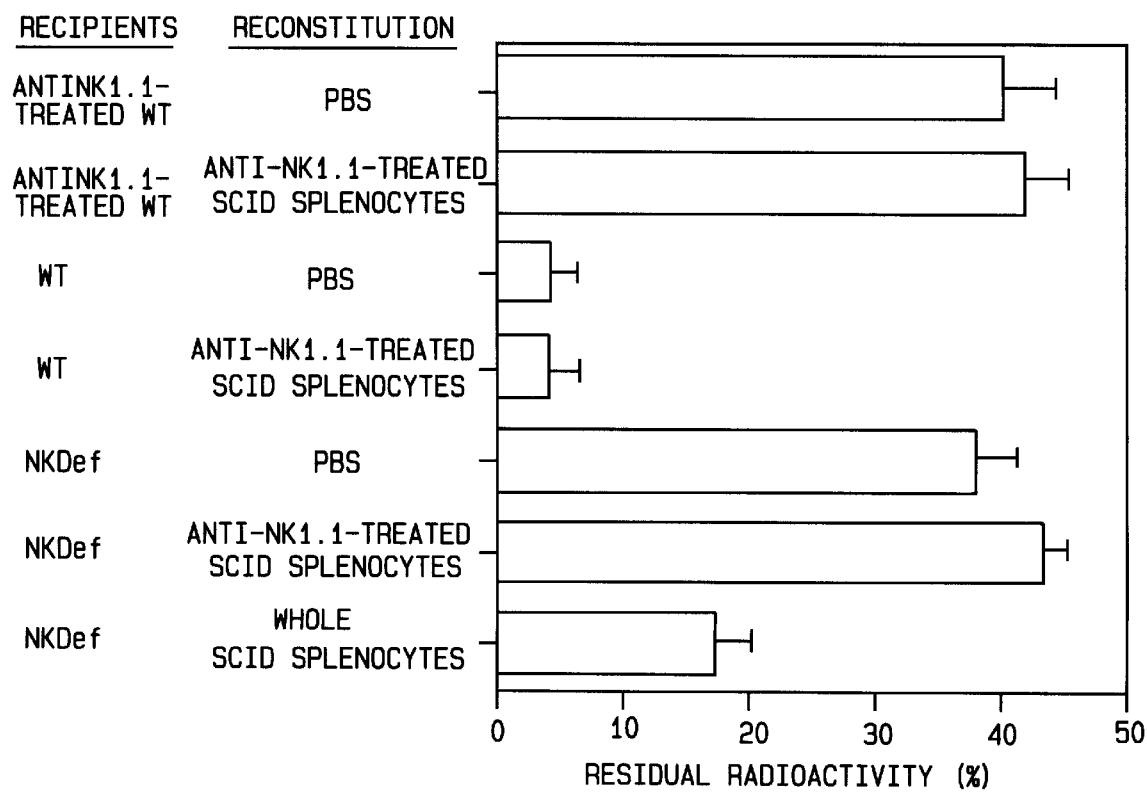
FIG. 7 is a graph which demonstrates that splenocytes from scid mice reconstitute acute in vivo tumor elimination in NKDef mice. Severe combined immunodeficiency (scid) mice that had been treated with anti-NK1.1 or untreated on day –2 were injected with poly-I:C on day –1. Two hrs after the intravenous infusion of $8 \times 10^6$ of untreated scid splenocytes, anti-NK1.1-treated scid splenocytes, or PBS, the recipient mice were injected intravenously with $3 \times 10^4$ RMA-S cells that were labeled with $^{125}$I-UdR. Six hrs later the residual radioactivity in the lungs was determined.

After transfer of scid spleen cells, the NKDef mice developed the capacity to eliminate tumors in vivo as detected by the lung clearance assay (FIG. 7). However, pretreatment of the scid mice with anti-NK1.1 mAb abrogated the capacity of scid splenocytes to restore tumor clearance. This provides further evidence that the functional defect in the NKDef mice is specifically due to a deficiency in NK cells and is not due to B or T cell dysfunction.

The NKDef phenotype appears to be due to an intrinsic defect in the NK cells themselves. Correlated with the functional deficiency of NK cells, there is a marked decrease in NK1.1$^+$ CD3$^-$ cells in the spleen, as detected by flow cytometry (FIG. 8). This population of cells has been previously correlated with NK cell function. Although there is a functional deficiency of NK cells in the spleen, peripheral blood, and lung (FIGS. 2–6), concomitant with a corresponding decreased number of NK1.1$^+$CD3$^-$ cells in the peripheral tissues (FIG. 8), there are more than twice the number of NK1.1$^+$CD3$^-$ cells in the bone marrow. These data suggest that there is a developmental abnormality of NK cells in NKDef mice.

Consistent with a developmental defect, the few peripheral NK1.1$^+$CD3$^-$ cells in NKDef mice (and the NK1.1$^+$ CD3$^-$ cells in the bone marrow) have abnormal expression of molecules found on mature, peripheral NK cells in normal mice. In particular, NK1.1$^+$CD3$^-$ cells express the β2 integrins LFA-1 (CD11a), Mac-1 (CD11b), and p150/95 (CD11c) (FIG. 9). The NK1.1$^+$CD3$^-$ cells from the NKDef mice express normal levels of LFA-1, indicating the integrity of the β2 integrin gene. However, NKDef cells fail to express Mac-1 and 150/95 (FIG. 9) even upon in vitro stimulation with phorbol ester which upregulates expression of these molecules on normal cells (data not shown) The NK1.1$^+$CD3$^-$ cells in the NKDef mice also do not express the B220 marker, whereas the NK1.1$^+$CD3$^-$ cells from wild type mice do express this marker (FIG. 9). As expected, nearly all NKDef NK1.1$^+$CD3$^-$ cells express Ly49A at intermediate levels.

Figure 12:
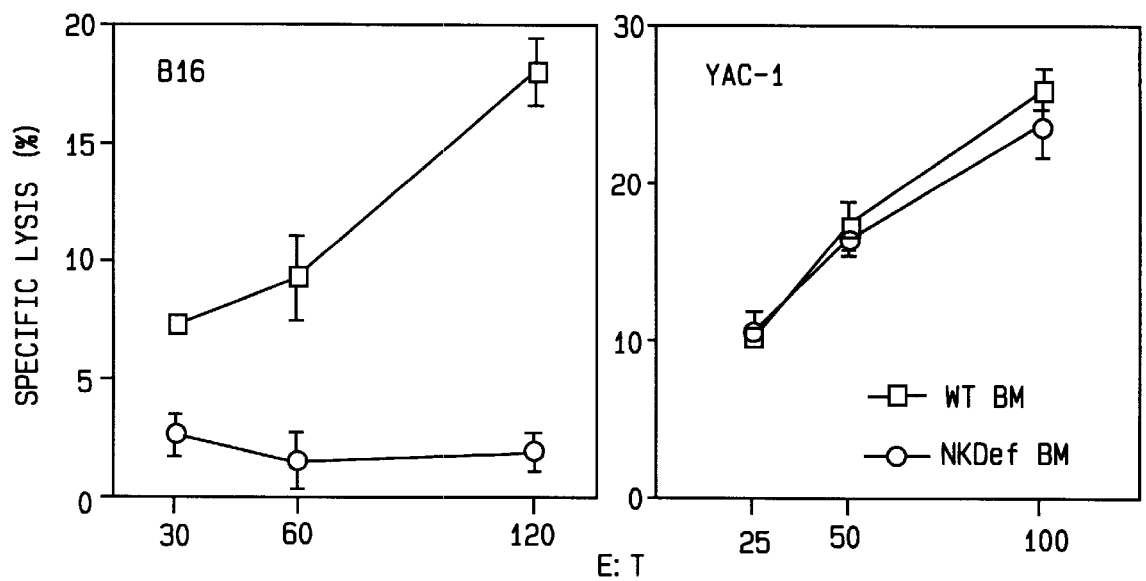
FIG. 12 is two graphs which demonstrate that bone marrow cells from NKDef mice manifest impaired in vitro natural killing against certain tumor cells. Wild-type (WT) and NKDef mice were injected interperitoneally with 150 μg poly-I:C. Twenty four hours later, the bone marrow cells were used in 4 hr $^{51}$Cr-release cytotoxicity assays against B16 and YAC-1 target cells at varying effector:target (E:T) ratios as indicated. Results are expressed as the mean percent-specific lysis±SD of triplicate wells.
Figure 13:
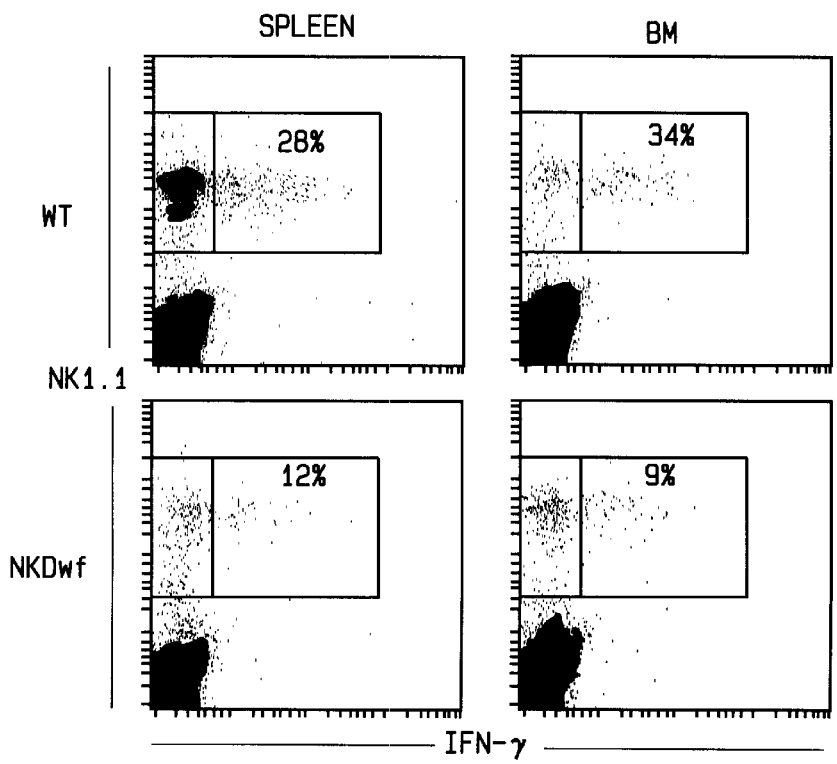
FIG. 13 is four graphs representing flow cytometry results which show the impaired capacity of NK1.1$^+$CD3$^-$ cells in NKDef mice to produce interferon-γ. Single cell suspensions were prepared from indicated organs and stimulated with IL-2 and IL-12 for 7 hr, with Brefeldin A during the last 4 hr. The cells were stained with Cy-conjugated anti-CD3 and PE-conjugated anti-NK1.1 antibodies, fixed, permeabilized, and subsequently stained with FITC-conjugated anti-interferon-γ antibody. Shown are profiles for interferon-γ production by cells gated on CD3-negative cell population in wild-type and NKDef mice. The numbers represent the percentage of cells producing interferon-γ among NK1.1$^+$ CD3$^-$ cells.

The remaining NK1.1$^+$CD3$^-$ cells from NKDef mice are also functionally impaired. For example, even though bone marrow cell preparations from NKDef mice contain greater numbers of NK1.1$^+$CD3$^-$ cells compared to wild-type mice (FIG. 8), their capacity to kill B16 tumor cells is greatly reduced (FIG. 12). Moreover, the levels of YAC-1 lysis are not increased over wild-type mice. Also, NK1.1$^+$CD3$^-$ cells in NKDef mice are impaired in their ability to produce interferon-γ (FIG. 13).

Figure 10B:
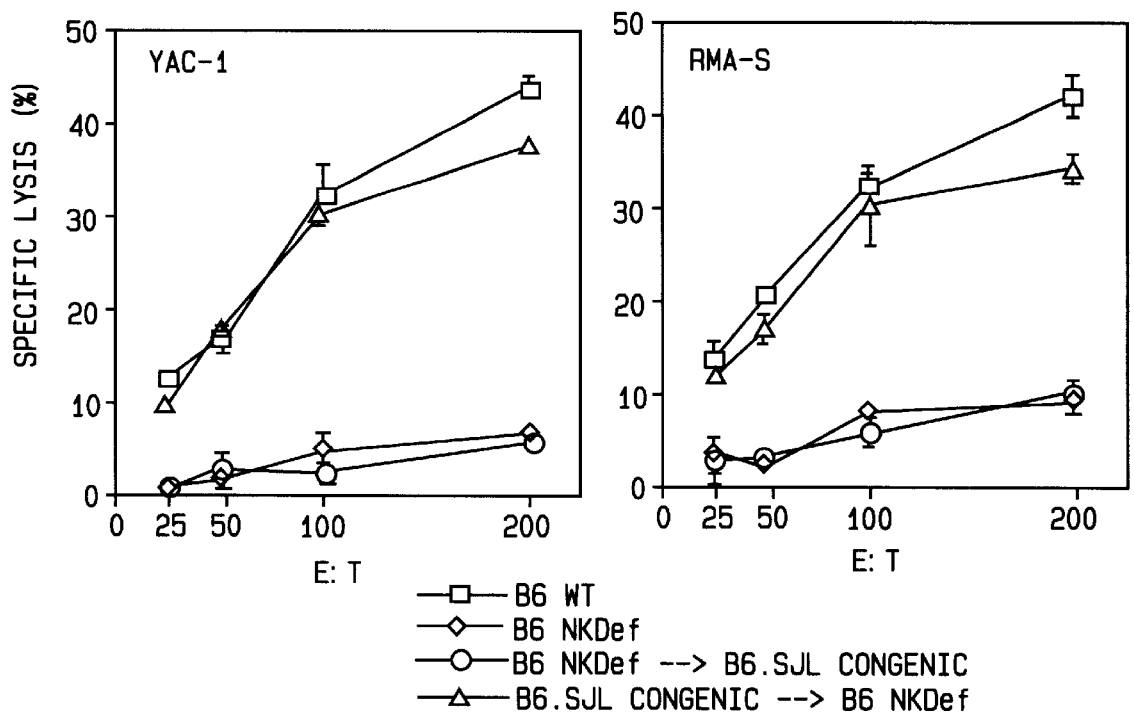
FIG. 10B shows poly-I:C-induced splenic NK activity against YAC-1 and RMA-S. The numbers represent the percentage of cells within the quadrant among all viable cells.

Bone marrow chimeric studies demonstrate that the NKDef defect is intrinsic to the NK cell lineage. Transfer of bone marrow cells from the NKDef mice into irradiated normal mice (congenic for Ly5 to permit identification of donor cells) does not yield donor NK1.1$^+$CD3$^-$ cells in the spleen (FIG. 10A) By contrast, normal bone marrow transferred to NKDef mice results in the production of donor NK1.1$^+$ CD3$^-$ spleen cells. Furthermore, splenic natural killing of YAC-1 and RMA-S tumor targets is restored when irradiated NKDef mice are reconstituted with normal bone marrow cells whereas transfer of NKDef bone marrow to normal recipients results in a deficiency in natural killing in vitro (FIG. 10B). Thus, NKDef mice have an NK cell lineage defect that is intrinsic rather than due to an alteration of host elements that indirectly affect NK cell development.

Figure 11:
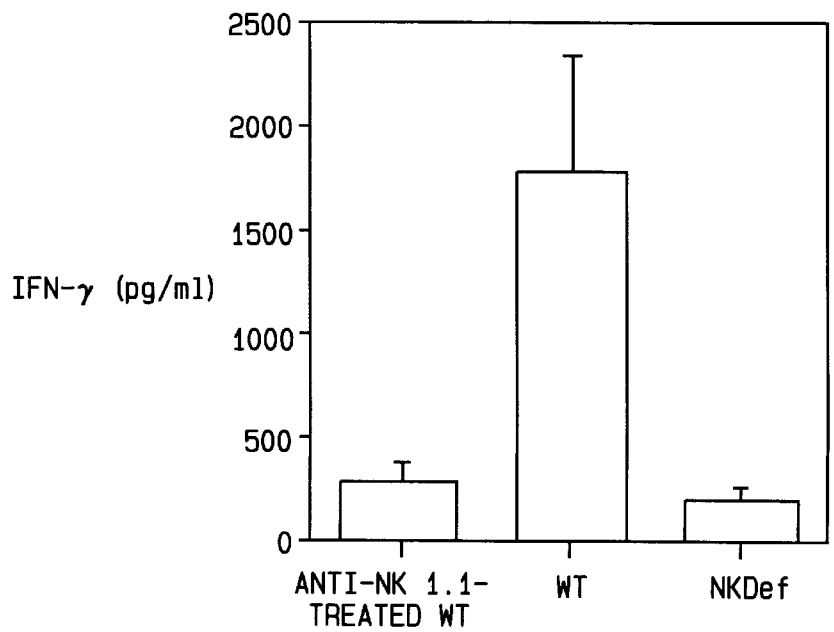
FIG. 11 is a graph which shows impaired in vivo interferon-γ production by NKDef mice in response to LPS. Mice were injected intraperitoneally with 20 μg E. coli LPS and bled 7 hr later. Serum interferon-γ levels were determined by ELISA. Results are represented as the mean±SD from 5 mice per group.

Although the NKDef mice have otherwise normal cellular constituents, they fail to produce interferon-γ when stimulated. In normal mice, injection of lipopolysaccharide (LPS) results in elevated interferon-γ levels in the peripheral blood, 7 hrs after administration (FIG. 11). However, in the NKDef mice, LPS administration fails to elicit interferon-γ production, suggesting that NK cells are the major source of interferon-γ when exogenous activators such as LPS are given.

Figure 15:
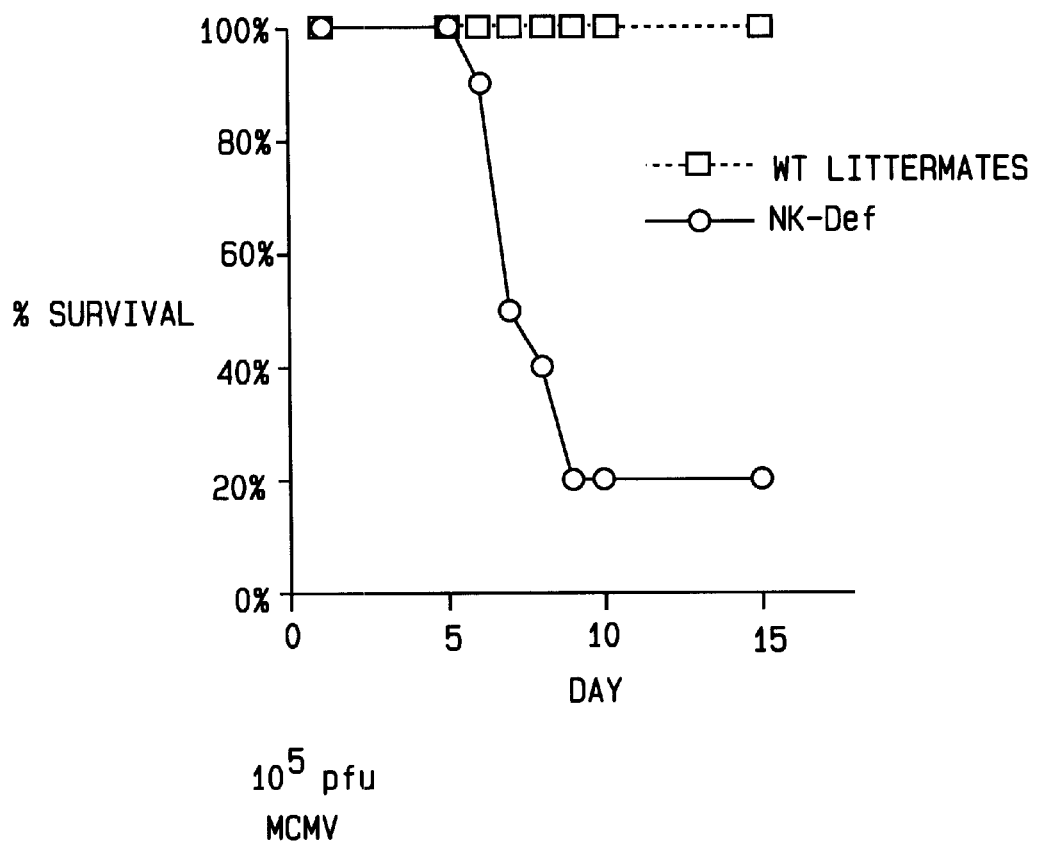
FIG. 15 is a graph which shows that NKDef mice have increased susceptibility to virus infection. Ten NKDef mice and 10 wild-type littermates were injected at day 0 with $10^5$ CFU cytomegalovirus. Survival of the mice was monitored for 15 d.

NKDef mammals are impaired in their ability to fight infection. For example, NKDef mice show defective immunity to cytomegalovirus (FIG. 15).

Use of NKDef Animals

Non-human mammals of the present invention are suitable for further evaluation of NK cell function and development. Enhanced understanding of NK cells leads to advances in the diagnosis and prevention of NK cell mediated human diseases. An example is the human disease characterized by a substantial deficiency in NK cells (38). This model is useful for studying the consequences of such a deficiency, such as susceptibility to viral infections, and for subsequent therapies. Moreover, by studying NK cells in isolation, strategies may be developed to specifically enhance NK cell activities, against tumors, for example. Agents may be injected that enhance NK cell activity in any of the described assays or other experiments to document NK cell activity. Candidate drugs that enhance immune responses in normal mice but fail to enhance immunity in the transgenic mice provide indications of agents that are NK cell specific agents. Such results may be confirmed and further studied in transgenic mice that are reconstituted with normal NK cell precursors.

The NKDef mice are useful in examining the role of NK cells in a large number of situations, including the influence of NK cells on specific immune responses. For example, the role of NK cells in regulating the development of specific immunity following vaccination is established by immunization of NKDef mice and comparison to normal mice, and NKDef mice reconstituted with NK cells. If NK cells promote specific immunity, agents that enhance NK cell activity will improve vaccination results.

Since NK cells are apparently involved in tumor surveillance, NKDef mice are useful to study the carcinogenic potential of any agent, thereby providing an animal model for toxicity testing. If the agent is a carcinogen, administration of the agent to the NKDef mice can result in the development of a tumor at lower doses and/or at earlier time periods than in normal mice. This is useful in screening agents for potential to cause diseases that are normally controlled by NK cells, since this control is unmasked in the NKDef mice.

The NKDef mice also provide a means to test and understand the immune response to microorganisms such as viruses, bacteria, and parasites. In particular, the role of NK cells in early phases of various infections can be determined, for example by comparing NKDef mice with mice with wild-type natural killer activity for their ability to fight infection with agents such as cytomegalovirus (see e.g. FIG. 15). Agents can also be tested to enhance NK cell clearance of the pathogens. Alternatively, human tissues could be used to reconstitute the mice such that agents can be tested to enhance human cellular function.

NK cells are implicated in autoimmune diseases such as rheumatoid arthritis (39). The apparent absence of NK cells is associated with marked exacerbation in animal models of induced autoimmune disease such as experimental allergic encephalomyelitis, a model of human multiple sclerosis (48). This dependency is further examined in other autoimmune diseases, such as animal models of systemic lupus erythematosus, rheumatoid arthritis, and diabetes mellitus. Agents that enhance NK cell activity provide new treatment modalities for these diseases. Moreover, the mice are useful for harboring human tissues that are affected by autoimmune diseases, and for testing agents to determine their efficacy in combating the autoimmune process. This may be done in a manner similar to adoptive tumor transfer, and the testing of anti-tumor agents may be carried out as described above.

Furthermore, the role of specific effector functions of NK cells can be studied. For example, perforin deficiency results in global inability to mediate lymphocyte cytotoxicity (26). This is due to the role of perforin in killing by cytotoxic T cells as well as NK cells. However, perforin-deficient NK cell precursors should not be able to reconstitute normal NK cell killing responses in the NKDef mice whereas cytotoxic T cell responses should be normal. For example, the transgenic mice can be reconstituted with NK cells from interferon-γ deficient mice. The reconstituted transgenic mice should then have NK cells that are capable of perforin and granzyme mediated cytotoxicity whereas NK cells will be deficient in interferon-y production. In addition, the reconstituted transgenic mice will have other cellular elements that should produce interferon-γ normally. In contrast, interferon-gamma deficiency results in interferon-γ production defects in every cell lineage. Similarly, the NKDef mice can be reconstituted with progenitor cells or NK cells from mice with other deficiencies, such that the NK cells that develop will have the defect because they are derived from the donor cells, but the other tissues and lymphoid cells will be normal because they are derived from the NKDef mice. Use of precursor cells from mice with targeted mutations in cytokine production or cytokine receptors will make it possible to study NK cell-mediated cytokine responses.

The transgenic mice are useful in further determining the role of NK cells in development and regulation of immune responses to pathogens, cancer, and vaccines. For example, through the production of interferon-γ, NK cells are thought to skew the development of T helper cell responses to the Th1 phenotype (40). This is tested in the transgenic mice in which normal responses may be reconstituted by transfer of NK cells from normal or immunodeficient mice that have NK cells. Furthermore, the mechanisms by which NK cells produce this effect is determined by testing individual effector functions by transfer of cytolytically impotent or cytokine-deficient NK cells as described above.

Furthermore, the same protocol is used to examine and establish developmental pathways if precursor cells are derived from mice that are deficient in signaling molecules, receptors, cytokines, or other molecules. The stage at which NK cell development is arrested can thus be determined so that a comprehensive view of the stages of NK cell development may be ascertained.

Because NK1.1$^+$CD3$^-$ cells from NKDef mice show a profoundly impaired ability to produce interferon-γ, and because these cells kill some, but not all, cancer cells which are killed by normal NK cells (Example 5), the study of these impaired NK cells is useful for elucidating the function of NK cells. By comparing the responses of normal NK cells with NK cells from NKDef mice, e.g., when exposed to cancer cells, the role of NK cells in, e.g., cancer immunity can be clarified.

Human NK cells may be used to reconstitute the transgenic mice, providing a means to study NK cells in the context of an otherwise normal immune system as well as to provide a means to study the function of human NK cells in isolation as described above. Moreover, their efficacy in eradicating infections or tumors could be tested.

The NKDef animals are useful to obtain a non-human mammal that is deficient in NK cells alone, NK and T cells, NK and B cells, or NK, T, and B cells. For this purpose, the NKDef animal, deficient in NK cells, is mated with an animal that has a selective deficiency in T cells. The progeny from that cross are preferably screened for the NKDef phenotype, and the UNKDef mice selected from that cross are backcrossed to the T cell deficient animals. Assuming that the T cell deficiency is a recessive character, and with no linkage between the NKDef phenotype and the T cell deficiency character, about ¼ of the mice resulting from this backcross will have the NKDef phenotype with a T cell deficiency. The preferred T cell deficient animal is a mouse with a mutation in the T cell receptor alpha gene (41). To obtain a NK and B cell deficient animal, the same mating and selection protocol as described above with T cell deficient animals is preferably followed (cross between the NKDef and B cell deficient animal, select for NKDef phenotype, backcross to B cell deficient animal, selection for animals with NKDef and B cell deficiency). The preferred B cell deficient animal is a mouse with a mutation in the mu (IgM) gene (42). To obtain a mouse deficient in NK, T, and B cells, the above mating and selection protocol is preferably performed with a NKDef animal and an animal that is deficient in T and B cells. The preferred T and B cell deficient animal is the severe combined immunodeficient (scid) mouse, arising from a spontaneous mutation, or mice with mutation in RAG-1 or RAG-2 genes (11, 43, 44). Alternatively, a NK, T, and B cell deficient animal may be obtained by sequential matings, selection and backcrossing of the NK cell deficient, the T cell deficient, and the B cell deficient animals, thus combining the three deficiencies in one animal.

When scid mice are mated to NKDef mice, and the NKDef progeny are selected, then backcrossed to scid mice, about one-quarter of the backcross progeny have a scid /NKDef phenotype. This indicates that the scid and the NKDef genetic loci are unlinked. While scid mice have approximately 10 times the number of NK cells (i.e. NK1.1$^+$ CD3$^-$ cells) as normal mice (about 25% of nucleated blood cells are NK cells in scid mice, compared to about 2.5% in normal mice), scid /NKDef mice have about 3.7% NK cells. See Example 6 and FIG. 14. The phenotype of the NK cells from scid /NKDef mice is the same as NKDef mice.

When RAG-1 mice are mated to NKDef mice, and the NKDef progeny are backcrossed to RAG-1 mice, the backcross progeny which are RAG-1/NKDef is about 2%, rather than the expected 25%. This indicates that the NKDef genetic locus is linked to the RAG-1 locus, on mouse chromosome 2 (map position 56.0). However, when NKDef mice are mated, selected, and backcrossed (as above) to mice deficient in β2-microglobulin (β2m$^{-/-}$), which is also located on mouse chromosome 2 but distal to the RAG-1 locus (map position 69.0), no linkage is evident from the ratios of the progeny which are β2m$^-$/NKDef. This indicates that the NKDef locus is linked to RAG-1 but far enough from the β2m locus to avoid any linkage effects. The RAG-1/NKDef mice which do result from the RAG-1 X NKDef mating has a phenotype like the scid /NKDef mice.

The NKDef mice are useful as hosts for foreign cells, such as human tissues or blood cells, including bone marrow. Due to the NK cell deficiency, the mice are capable of harboring xenografts, either by themselves or when the NKDef mice are bred to contain other immunodeficiencies. In an advance, the NKDef mice do not need to be injected with antibodies to eliminate NK cells. Since the human cells are not rejected, the human cells should grow and be amenable to further study.

The human tissues can be transplanted into NKDef by methods known in the art. For example, a blood cell suspension can be injected intravenously or intraperitoneally. Human tissues may also be implanted subcutaneously, under a muscle, or under the kidney capsule.

The human tissues may arise from normal individuals or patients with diseases such as tumors, hematopoietic malignancies, autoimmune diseases such as systemic lupus erythematosus, rheumatoid arthritis, Sjogren's syndrome, inflammatory myositis, spondyloarthropathies, vasculitis, sarcoidosis, cryoglobulinemia, diabetes mellitus, and inflammatory bowel disease. The human tissues, growing in the immunodeficient mice may be further studied for such effects as their response to growth factors and drugs to determine efficacy of new treatments. The human tissues may also be susceptible to infection with human pathogens. Drugs or potential therapeutic agents could thus be administered to test efficacy in ameliorating disease or to determine drug toxicity. Furthermore, the mice may be used to further functional and molecular characterization that could lead to determination of the etiology and pathogenesis of disease.

For diagnostic purposes, the transfer of human cells to NKDef mice permits exploration of microorganisms that infect human tissues. This is especially helpful in situations where it is difficult to culture the microorganism by other methods, or to provide the methodology to initially identify a causative microorganism in diseases in which microorganisms are presumed to be causative agents but have not yet been identified because of inability to culture the microorganisms in vitro. For example, serial transfer of tissues from NKDef mice containing diseased human tissues to transgenic mice with normal human tissues can provide evidence in support of infectious etiologies that can be isolated.

The NKDef animal serves as a model with which to study tissue transplantation and to determine the efficacy of therapies that modify selected lymphocytes. In this respect, the method involves the use of NK immunodeficient mice with or without other immunodeficiencies that are transplanted with tissues from various different organs or human tissues. Human cells responsible for transplant rejection may also be administered and therapies to alter transplant rejection may be tested for efficacy.

The following examples illustrate the invention, but are not to be taken as limiting the various aspects of the invention so illustrated.

EXAMPLES

Materials

Mice. C57BL/6, C57BL/6-Prkdcscid/Sz, C57BL/6-Rag1−/−, B6.SJL-PtprcaPepb/Boy (Ly5.1), and C57BL/6-B2m−/− mice were obtained from the Jackson Laboratory (Bar Harbor, Me.) and maintained in a specific pathogen free facility at Washington University (St. Louis, Mo.).

Cell Lines. YAC-1 (Moloney virus-transformed A/Sn-derived T cell lymphoma) was obtained from the American Type Culture Collection (ATCC; Rockville, Md.). RMA-S is a Tap-2-deficient mutant originated from RBL-5 (Rauscher virus-induced C57BL/6-derived T lymphoma) and was provided by Dr. Klas Karre (Karolinska Institute, Stockholm, Sweden). B16 (spontaneous C57BL/6-derived melanoma) was obtained from Dr. William Seaman (University of California, San Francisco, Calif.). Cells were grown in RPMI 1640 medium (Gibco, Grand Island, N.Y.) supplemented with 10% fetal calf serum (FCS; Harlan, Indianapolis, Ind.), L-glutamine (300 μg/ml), penicillin (100 U/ml), streptomycin (100 μg/ml) and 50 μM β-mercaptoethanol (hereafter referred to as complete RPMI-10 medium).

Antibodies and Reagents. Hybridomas producing the following mAbs were obtained from ATCC: Anti-NK1.1 (PK136), anti-rat K (MAR 18.5) and anti-FcγRII/III (2.4G2). These mAbs were purified from hybridoma culture supernatants by standard methods. The following mabs were purchased from Pharmingen (San Diego, Calif.); phycoerythrin (PE)-conjugated anti-NK1.1 (PK136), fluorescein isothiocyanate (FITC) or Cy-Chrome (CyC)-conjugated anti-CD3e (145-2C11), FITC-conjugated anti-CD4 (GK1.5), FITC-conjugated anti-CD8 (53-6.7), FITC-conjugated anti-CD11a (2D7), FITC-conjugated anti-CD11b (M1/70), FITC-conjugated anti-CD11c (HL3) and FITC-conjugated anti-interferon-γ (XMG1.2) . FITC-conjugated F(ab')$_2$ fragment of goat anti-mouse Ig antibody was purchased from Cappel Inc. (Malvern, Pa.). Anti-Ly-49A (JR9-318) was obtained from Dr. J. Roland (Pasteur Institute, Paris, France) and conjugated to FITC by standard methods. Human recombinant IL-2 was purchased from Chiron (Emeryville, Calif.). Polyinosinic-polycytidylic acid (poly-I:C), lipopolysaccharide (LPS; *Escherichia coli* serotype 0127:B8) and Percoll were purchased from Sigma (St. Louis, Mo.). Lympholyte-M was purchased from Cederlane (Westbury, N.Y.).

Example 1

Generation of NKDef Mice

The murine granzyme A genomic DNA was obtained from Drs. H. Aguila and Irving Weissman (Stanford University, Stanford, Calif.) and used for the in vivo expression of Ly-49A. Since little is known about the sequences regulating tissue specific expression of granzyme A, the entire genomic sequence (carrying 11 kb putative promoter and 7 kb structural gene with poly-A addition signal, FIG. 1) (45) was used as an expression cassette. The granzyme A-Ly-49A transgene was constructed by standard methods. To facilitate the expression of Ly-49A, the translation start codon of granzyme A gene was deleted by replacing 1032 bp NaeI-SmaI fragment (carrying the putative promoter and start codon) with a truncated 1008 bp NaeI-SmaI fragment (carrying only the putative promoter) generated by PCR using the primers CCTGAAGCATGCTATCTCACGA (SEQ 1D 70:1), and GTTCCCGGGCTCTCCCAC-CCCAATCA (SEQ 1D 70:2). The Ly-49A cDNA was excised as an 1.2 kb XhoI fragment from pA1.3 (32), filled by Klenow treatment, and inserted into the SmaI site of the modified granzyme A gene. The granzyme A-Ly-49A transgene was excised as 19 kb SalI-KpnI fragment and microinjected into the pronucleus of a fertilized C57BL/6 egg by standard methods (33). Initial screening for transgenic mice was performed by Southern blot analysis of tail DNA with the Ly-49A cDNA probe. To examine the expression of the transgenic Ly-49A, single drops of blood were obtained from candidate mice at the time of tail harvest. The blood was cultured in single wells of a 96 well sterile microtiter plate with RPMI 1640 media containing 10% fetal calf serum and recombinant human IL-2 (1000 U/ml) for 10d. Cell surface expression of Ly49A was determined by flow cytometry analysis; Ly-49A was expressed on nearly all IL-2-expanded cells from transgenic mice whereas it was expressed on only a subpopulation (about 20%) of IL-2-expanded cells from non-transgenic mice. After transgenic founder lines were established, transgenic mice were screened by PCR analysis of tail DNA using Ly-49A cDNA-specific primers.

The initial microinjection of fertilized eggs yielded 42 pups. Seven were found by Southern blot to have the transgene. Three expressed the transgene, as established by blood drop analysis. One of the three that expressed the transgene could not transmit the transgene to its offspring. Another one of the three expressed the transgene weakly. The last of the three expressed the transgene and the NKDef phenotype.

A second microinjection experiment yielded 40 pups. Only one contained the transgene by PCR. That mouse expresses the transgene on a subpopulation of NK cells.

A third microinjection experiment yielded 12 pups. Only one of those pups contained the transgene by PCR. That mouse expresses the transgene on a subpopulation of NK cells.

The genome of the mouse that has the NKDef phenotype contained about 30 copies of the transgenic construct.

Example 2

Evaluation of Tumor Cytotoxicity

Cell preparation. Under metofane anesthesia, mice were exsanguinated by cardiac puncture then spleen, liver, lung and bone marrow were collected. Cell suspensions from spleen and bone marrow were prepared by passage through sieves in HBSS (Gibco) containing 10% FCS and red blood cells (RBCs) were lysed with RBC lysis solution (0.14 M $NH_4Cl$ and 0.017 M Tris, pH 7.2). Cell suspensions from liver and lung were prepared in HBSS without FCS and subsequently hepatic and lung mononuclear cells (MNC) were isolated by centrifugation on 30% Percoll gradient in the presence of heparin (50 IU/ml). The pellets were resuspended in RBC lysis solution. Peripheral blood was directly treated with RBC lysis solution. After RBC lysis, remaining cells in all preparations were washed with RPMI 1640 medium containing 10% FCS.

In vitro Cytotoxicity Assay. NK cell activity was boosted by peritoneal injection of poly-I:C (150 $\mu$g) into experimental mice. 24 h later, splenocyte and bone marrow cell suspensions were prepared as described above and natural killing was tested by standard $^{51}Cr$-release assay (46). Briefly, YAC-1, RMA-S, or B16 tumor target cells ($3 \times 10^6$) were radiolabeled with 100 $\mu$Ci of $Na_2{}^{51}CrO_4$ (Amersham, Arlington Heights, Ill.) in complete RPMI-10 medium for 90 min at 37° C., washed three times in complete RPMI-10 medium, and plated at a constant cell number ($10^4$ cells/well) into 96 well round-bottom plates. Splenocytes or bone marrow cells were added to the wells at various cell densities in order to achieve effector-to-target (E:T) ratios of 25:1, 50:1, 100:1 and 200:1. After 4 hr incubation at 37° C., supernatant was collected and radioactivity was counted with a gamma counter. The percentage of specific cytotoxicity was calculated according to the standard formula: % specific lysis=100× (Experimental–Spontaneous)/( Total–Spontaneous) where "Experimental" represents the radioactivity from experimental wells, "Spontaneous" represents the radioactivity from wells with targets alone, and "Total" represents the radioactivity obtained from detergent (2% Triton-X100) lysed targets.

FIG. 2 shows that splenocytes from NKDef mice killed less than 10% of the tumor target cells, even at the highest E:T ratio of 200. By contrast, splenocytes from the wild type mice killed 30–50% of the tumor target cells.

Acute in vivo Tumor Rejection Assay. YAC-1 or B16 tumor cells ($8 \times 10^6$) were incubated with 50 $\mu$g of 5-fluoro-2-deoxyuridine (FUdr; Sigma) in 2 ml of complete DMEM (Gibco) medium containing 10% FCS for 15 min at 37° C. 10 $\mu$Ci of $^{125}I$-labeled 5-iodo-2-deoxyuridine ($^{125}I$-Udr; Amersham, Arlington Heights, Ill.) was added for an additional 2 hr incubation at 37° C. Cells were washed three times in PBS. Mice were injected intravenously through tail vein with $3 \times 10^4$, $1 \times 10^5$ or $3 \times 10^5$ tumor cells in 200 $\mu$l volume of PBS. 4 to 8 hr after injection, mice were sacrificed and the lungs were removed, rinsed with PBS then soaked in 70% ethanol for 1 hr. Residual radioactivity in the lungs was counted with a gamma counter. The percentage of residual radioactivity was calculated as follows: % residual radioactivity=(residual radioactivity in the lungs/total injected radioactivity)×100.

FIG. 3 shows that the NKDef mice were similar to the anti-NK1.1-treated wild type mice in their inability to reject tumor cells, whereas the wild type mice were able to effectively reject the tumor cells. The ability of transplanted splenocytes from scid mice to restore the tumor rejection ability of NKDef mice is demonstrated in FIG. 7.

Intermediate and Long-Term in vivo Tumor Rejection Assay. For tumor metastases and intermediate in vivo growth assay, mice were injected intravenously through tail vein with $3 \times 10^4$ B16 melanoma cells in 200 $\mu$l volume of PBS. 14 d later, the lungs were removed and visible, macroscopic black metastatic foci were counted. For long term tumor outgrowth assay, mice were injected subcutaneously in the left flank with $1 \times 10^2$ to $1 \times 10^5$ RMA-S cells in 100 $\mu$l volume of RPMI 1640. Mice were monitored for palpable tumors twice weekly. Mice without tumors were observed for at least 9 weeks.

FIG. 4 shows that the wild type mice effectively prevented lung metastases, while the NKDef and anti-NK1.1-treated wild type mice were greatly impaired in prevention of metastases. Similarly, FIG. 5 shows that the NKDef mice were unable to prevent long-term tumor formation, since all of the NKDef mice developed palpable tumors, even at the lowest dosage of tumor cells. By contrast, the wild type mice were much more able to prevent long-term tumor development.

Example 3

Bone Marrow Graft Rejection and Generation of Bone Marrow Chimeras

After otherwise lethal γ irradiation (9.5 Gy from a $^{137}Cs$ source) on day 0, recipient mice were transplanted with $5 \times 10^5$ to $5 \times 10^6$ bone marrow cells (BMC) from indicated donor mice via intravenous tail vein injection, as previously described (47). For the BMC graft rejection assay, on day 5, recipient mice were injected intravenously with 3 $\mu$Ci of $^{125}I$-Udr and $1 \times 10^{-11}$ M of FUdr. On day 6, the spleens were removed, rinsed with PBS and the radioactivity was counted with a gamma counter. Radioactivity incorporation into the spleens was used as an index of hematopoietic precursor cell proliferation. For the construction of bone marrow chimeric mice, recipient mice were kept for 8 to 12 weeks until analysis.

FIG. 6 shows that, unlike the wild type mice, the NKDef mice were unable to reject bone marrow cells from $\beta 2m^{-/-}$ mice.

Example 4

Determination of Lymphocyte Constituents

Flow Cytometry. For the phenotyping of marker expression, cells were incubated with anti-FcγRII/III antibody to block non-specific binding of fluorochrome-conjugated antibodies then stained with combinations of appropriate fluorochrome-conjugated antibodies. Stained cells were analyzed with a FACScalibur (Becton Dickinson, Mountain View, Calif.). Dead cells were removed by centrifugation on Lympholyte-M gradient or excluded from analysis by propidium iodide staining.

FIG. 8 shows that the NKDef mice had a marked decrease in the NK phenotype NK1.1$^+$CD3$^-$ cells in all tissues except the bone marrow, which had an increase in cells of that phenotype. FIG. 9 shows that the few peripheral cells which have the NK1.1$^+$CD3$^-$ phenotype have an unusual phenotype with respect to other cell surface markers.

Example 5

Functional Characteristics of NK1.1+CD3− Cells from NKDef Mice

In vivo Interferon-γ Production in Response to Lipopolysaccharide. In order to assess interferon-γ production in vivo, mice were injected with 20 μg of E. coli-derived lipopolysaccharide. Seven hr later, blood was collected by heart puncture and serum levels of interferon-γ were determined using an interferon-γ ELISA kit (Endogen, Woburn, Mass.) according to the manufacturer's instructions. FIG. 11 shows that the NKDef and anti-NK1.1-treated wild-type mice are impaired in lipopolysaccharide-induced interferon-γ production, while wild-type mice produced significant amounts of interferon-γ.

In vitro Interferon-γ Production by NK1.1$^+$CD3$^-$ cells. In order to evaluate the functional activity of the NK1.1$^+$CD3$^-$ cells in NKDef mice, the interferon-γ production of each cell with that phenotype was examined by flow cytometric analysis following intracellular staining of interferon-γ. Whole splenocytes and bone marrow cells were isolated from untreated mice and stimulated at a concentration of 1×10$^6$ cells/ml for 7 hr in the presence of both IL-2 (1000 U/ml) and IL-12 (10 ng/ml). To accumulate interferon-γ within the cells, the protein transport inhibitor Brefeldin A (Sigma Chemical Co., St. Louis, Mo.) was added into the culture for the last 4 hr. The cells were first stained with Cy-conjugated anti-CD3 and PE-conjugated anti-NK1.1 antibodies, then stained for intracellular interferon-γ with FITC-conjugated anti-interferon-γ antibody using the Cytofix/Cytoperm Plus™ Kit (Pharmingen) according to the manufacturer's instructions. Briefly, the cells were fixed with fixation buffer containing 4% paraformaldehyde for 20 min, washed twice with permeabilization buffer containing 0.1% saponin, and incubated with FICT-conjugated anti-interferon-γ in the presence of 0.1% saponin for 30 min. Stained cells were washed twice and analyzed with a FACSCalibur as described above.

FIG. 13 shows that both splenic and bone marrow NK1.1$^+$CD3$^-$ cells remaining in NKDef mice are impaired in interferon-γ production in response to IL-2 and IL-12. Compared to corresponding cells in wild-type mice, the levels of interferon-γ produced by the NK1.1$^+$CD3$^-$ cells remaining in NKDef mice were much lower, and the frequency of cells producing interferon-γ was reduced by 50–75%.

The NKDef NK1.1$^+$CD3$^-$ bone marrow cells were also tested for their ability to kill tumor cells in vitro, using the in vitro cytotoxicity assay method described in Example 2. As shown in FIG. 12, despite having a greater of NK1.1$^+$CD3$^-$ cells, bone marrow cell preparations from NKDef mice did not exhibit increased killing of B16 and YAC-1 tumor cells.

Example 6

Generation of Severe Combined Immunodeficient (scid)-NKDef Mice

NKDef mice were bred with C57BL/6-scid mice. F1 heterozygous NKDef mice were screened by PCR analysis of tail DNA as described above and backcrossed with scid mice. F2 offspring from this backcross were screened for the NKDef and scid phenotypes, for example the lack of CD3-positive T cells, by flow cytometric analysis of peripheral blood. Mice with both the scid and the NKDef (scid-NKDef) phenotypes were selected.

Figure 14:
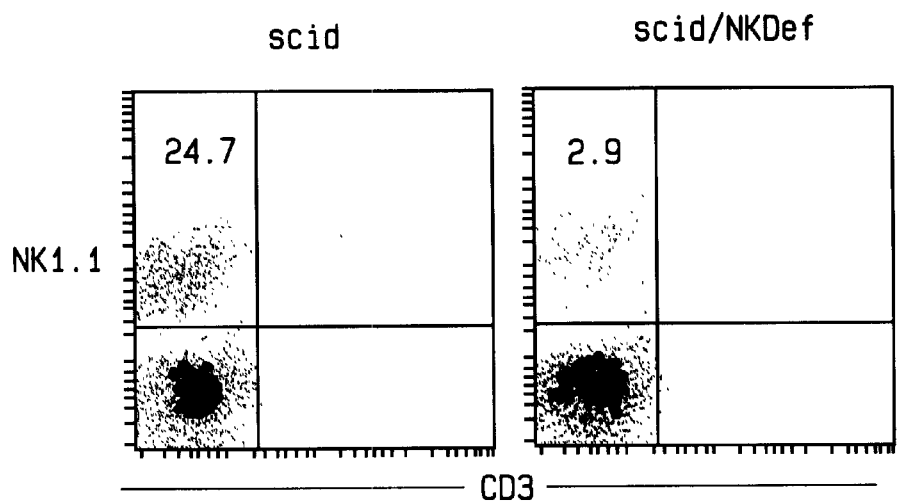
FIG. 14 is two graphs representing flow cytometry results which demonstrate the marked decrease in peripheral NK1.1$^+$CD3$^-$ cells in scid-NKDef mice. After removal of red blood cells, remaining blood cells were subjected to dual staining with PE-conjugated anti-NK1.1 and FITC-conjugated anti-CD3 antibodies. The numbers represent the percentage of cells within the quadrant among all viable cells.

FIG. 14 shows that the number of peripheral NK1.1$^+$CD3$^-$ cells was markedly reduced in scid-NKDef mice compared to non-NK deficient littermate scid mice.

Example 7

Susceptibility of NKDef Mice to Virus Disease

Ten NKDef mice and 10 wild-type littermates of the NKDef mice were each infected with 10$^5$ CFU cytomegalovirus according to the methods of Scalzo et al. (49). As shown in FIG. 15, all of the wild-type mice survived, but only 20% of the NKDef mice survived. This demonstrates that functional natural killer cells contribute to viruses immunity, and that NKDef mice lack a significant portion of that function.

Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

REFERENCES

1. Trinchieri, G. 1989. Biology of natural killer cells. Adv. Immunol. 47: 187–376
2. Bancroft, G. J. 1993. The role of natural killer cells in innate resistance to infection. Curr. Opin. Immunol. 5: 503–10
3. Janeway, C. A., Jr., P. Travers. 1997. Immunobiology. The immune system in health and disease. Third ed. London: Current Biology
4. Hackett, J., Jr., G. C. Bosma, M. J. Bosma, M. Bennett, V. Kumar. 1986. Transplantable progenitors of natural killer cells are distinct from those of T and B lymphocytes. Proc. Natl. Acad. Sci. U.S.A. 83:3427–31
5. Wilder, J. A., C. Y. Koh, D. Yuan. 1996. The role of NK cells during in vivo antigen-specific antibody responses. J. Immunol. 156:146–52
6. Murphy, W. J., V. Kumar, M. Bennett. 1987. Rejection of bone marrow allografts by mice with severe combined immune deficiency (scid). Evidence that natural killer cells can mediate the specificity of marrow graft rejection. J. Exp. Med. 165: 1212–1217
7. Lin, Y., M. Vandeputte, M. Waer. 1997. Natural killer cell- and macrophage-mediated rejection of concordant xenografts in the absence of T and B cell responses. J. Immunol. 158: 5658–67
8. Suttles, J., G. A. Schwarting, R. D. Stout. 1986. Flow cytometricanalysis reveals the presence of asialo GM1 on the surface membrane of alloimmune cytotoxic T lymphocytes. J. Immunol. 136: 1586–91
9. Koo, G. C., F. J. Dumont, M. Tutt, J. Hackett, Jr., V. Kumar. 1986. The NK-1.1 (−) mouse: a model to study differentiation of murine NK cells. J. Immunol. 137: 3742–7
10. Cui, J. Q., T. Shin, T. Kawano, H. Sato, E. Kondo, I. Toura, Y.Kaneko, H. Koseki, M. Kanno, M. Taniguchi.

1997. Requirement for Va14NKT Cells in IL-12-mediated rejection of tumors. Science. 278:1623–1626
11. Lieber, M. R., U. Grawunder, X. Wu, M. Yaneva. 1997. Tying loose ends: roles of Ku and DNA-dependent protein kinase in the repair of double-strand breaks. Current Opinion in Genetics & Development. 7:99–104
12. Smart, B. A., H. D. Ochs. 1997. The molecular basis and treatment of primary immunodeficiency disorders. Current Opinion in Pediatrics. 9: 570–6
13. Sandhu, J. S., E. Boynton, R. Gorczynski, N. Hozumi. 1996. The use of scid mice in biotechnology and as a model for human disease. Critical Reviews in Biotechnology. 16: 95–118
14. Barbosa, M. D., Q. A. Nguyen, V. T. Tchernev, J. A. Ashley, J. C. Detter, S. M. Blaydes, S. J. Brandt, D. Chotai, C. Hodgman, R. C.Solari, M. Lovett, S. F. Kingsmore. 1996. Identification of the homologous beige and Chediak-Higashi syndrome genes. Nature. 382:262–5
15. Shultz, L. D., P. A. Schwitzer, T. V. Rajan, T. L. Yi, J. N. Ihle, R. J. Matthews, M. L. Thomas, D. R. Beier. 1993. Mutations at the murine motheaten locus are within the hematopoietic cell protein-tyrosine phosphatase (Hcph) gene. Cell. 73: 1445–1454
16. Suzuki, H., G. S. Duncan, H. Takimoto, T. W. Mak. 1997. Abnormal development of intestinal intraepithelial lymphocytes and peripheral natural killer cells in mice lacking the IL-2 receptor beta chain. J. Exp. Med. 185: 499–505
17. DiSanto, J. P., W. Muller, D. Guy-Grand, A. Fischer, K. Rajewsky. 1995. Lymphoid development in mice with a targeted deletion of the interleukin 2 receptor gamma chain. Proc. Natl. Acad. Sci. U.S.A. 92: 377–81
18. Mackarehtschian, K., J. D. Hardin, K. A. Moore, S. Boast, S. P. Goff, I. R. Lemischka. 1995. Targeted disruption of the flk2/flt3 gene leads to deficiencies in primitive hematopoietic progenitors. Immunity. 3: 147–61
19. Georgopoulos, K., M. Bigby, J. H. Wang, A. Molnar, P. Wu, S.Winandy, A. Sharpe. 1994. The Ikaros gene is required for the development of all lymphoid lineages. Cell. 79: 143–56
20. Ohteki, T., H. Yoshida, T. Matsuyama, G. S. Duncan, T. W. Mak, P. S. Ohashi. 1998. The transcription factor interferon regulatory factor1 (IRF-1) is important during the maturation of NK1.1+T cell receptor-ab+ (NK1+T) cells, natural killer cells, and intestinal intraepithelial T cells. J. Exp. Med. 187: 967–972
21. Barton, K., N. Muthusamy, C. Fischer, C. N. Ting, T. L. Walunas, L. L. Lanier, J. M. Leiden. 1998. The Ets-1 transcription factor is required for the development of natural killer cells in mice. Immunity 9:555–63.
22. Yokota, Y., A. Mansouri, S. Mori, S. Sugawara, S. Adachi, S. Nishikawa, P. Gruss. 1999. Development of peripheral lymphoid organs and natural killer cells depends on the helix-loop-helix inhibitor Id2. Nature 397:702–6.
23. Wang, B., C. Biron, J. She, K. Higgins, M. J. Sunshine, E. Lacy, N. Lonberg, C. Terhorst. 1994. A block in both early T lymphocyte and natural killer cell development in transgenic mice with high-copy numbers of the human CD3E gene. Proc. Natl. Acad. Sci. U.S.A. 91:9402–6
24. Suwa, H., T. Tanaka, F. Kitamura, T. Shiohara, K. Kuida, M.Miyasaka. 1995. Dysregulated expression of the IL-2 receptor beta-chain abrogates development of NK cells and Thy-1+ dendritic epidermal cells in transgenic mice. Int. Immunol. 7: 1441–9
25. Aguila, H. L., I. L. Weissman. 1996. Hematopoietic stem cells are not direct cytotoxic targets of natural killer cells. Blood. 87:1225–31
26. Lowin, B., F. Beermann, A. Schmidt, J. Tschopp. 1994. A null mutation in the perforin gene impairs cytolytic T lymphocyte- and natural killer cell-mediated cytotoxicity. Proc. Natl. Acad. Sci. U.S.A. 91: 11571–5
27. Ebnet, K., M. Hausmann, F. Lehmann-Grube, A. Mullbacher, M. Kopf, M. Lamers, M. M. Simon. 1995. Granzyme A-deficient mice retain potent cell-mediated cytotoxicity. EMBO Journal. 14: 4230–9
28. Takai, T., M. Li, D. Sylvestre, R. Clynes, J. V. Ravetch. 1994. FcR gamma chain deletion results in pleiotropic effector cell defects. Cell. 76: 519–29
29. Takeda, K., H. Tsutsui, T. Yoshimoto, O. Adachi, N. Yoshida, T. Kishimoto, H. Okamura, K. Nakanishi, S. Akira. 1998. Defective NK cell activity and Th1 response in IL-18-deficient mice. Immunity. 8:383–390
30. Paine-Murrieta, G. D., C. W. Taylor, R. A. Curtis, M. H. Lopez, R. T. Dorr, C. S. Johnson, C. Y. Funk, F. Thompson, E. M. Hersh. 1997. Human tumor models in the severe combined immune deficient (scid) mouse. Cancer Chemotherapy & Pharmacology. 40: 209–14
31. Moffat, J. F., L. Zerboni, P. R. Kinchington,. C. Grose, H. Kaneshima, A. M. Arvin. 1998. Attenuation of the vaccine Oka strain of varicella-zoster virus and role of glycoprotein C in alphaherpesvirus virulence demonstrated in the SCID-hu mouse. J. Virol. 72: 965–74
32. Yokoyama, W. M., L. B. Jacobs, O. Kanagawa, E. M. Shevach, D. I. Cohen. 1989. A murine T lymphocyte antigen belongs to a supergene family of type II integral membrane proteins. J. Immunol. 143: 1379–86
33. Hogan, B., R. Beddington, F. Costantini, E. Lacy. 1994. Manipulating the mouse embryo: Cold Spring Harbor Laboratory Press
34. Yokoyama, W. M. in press. Chapter. Natural killer cells. Fourth ed. In Fundamental Immunology, ed. W. E. Paul. New York: Raven
35. Hackett, J., Jr., M. Bennett, V. Kumar. 1985. Origin and differentiation of natural killer cells. I. Characteristics of a transplantable NK cell precursor. J. Immunol. 134: 3731–8
36. Bix, M., N. S. Liao, M. Zijlstra, J. Loring, R. Jaenisch, D. Raulet. 1991. Rejection of class I MHC-deficient haemopoietic cells by irradiated MHC-matched mice. Nature. 349: 329–31
37. Bendelac, A., O. Lantz, M. E. Quimby, J. W. Yewdell, J. R. Bennink, R. R. Brutkiewicz. 1995. CD1 recognition by mouse NK1+T lymphocytes. Science. 268: 863–5
38. Biron, C. A., K. S. Byron, J. L. Sullivan. 1989. Severe herpesvirus infections in an adolescent without natural killer cells. N. Engl. J. Med. 320: 1731–5
39. Tak, P. P., J. A. Kummer, C. E. Hack, M. R. Daha, T. J. Smeets, G. W. Erkelens, A. E. Meinders, P. M. Kluin, F. C. Breedveld. 1994. Granzyme-positive cytotoxic cells are specifically increased in early rheumatoid synovial tissue. Arthritis Rheum. 37: 1735–43
40. Locksley, R. M. 1993. Interleukin 12 in host defense against microbial pathogens. Proc. Natl. Acad. Sci. U.S.A. 90: 5879–80
41. Mombaerts, P., A. R. Clarke, M. A. Rudnicki, J. Iacomini, S. Itohara, J. J. Lafaille, L. Wang, Y. Ichikawa, R. Jaenisch, M. L. Hooper, et al. 1992. Mutations in T-cell antigen receptor genes alphaand beta block thymocyte development at different stages. Nature. 360:225–31
42. Kitamura, D., J. Roes, R. Kuhn, K. Rajewsky. 1991. A Bcell-deficient mouse by targeted disruption of the membrane exon of the immunoglobulin mu chain gene. Nature. 350: 423–6
43. Shinkai, Y., G. Rathbun, K. P. Lam, E. M. Oltz, V. Stewart, M. Mendelsohn, J. Charron, M. Datta, F. Young, 43. A. M. Stall, et al. 1992. RAG-2-deficient mice lack mature lymphocytes owing to inability to initiate V(D)J rearrangement. Cell. 68: 855–67
44. Mombaerts, P., J. Iacomini, R. S. Johnson, K. Herrup, S. Tonegawa, V. E. Papaioannou. 1992. RAG-1-deficient mice have no mature P and T lymphocytes. Cell. 68: 869–877.
45. Hershberger, R. J., H. K. Gershenfeld, I. L. Weissman, L. Su.1992. Genomic organization of the mouse granzyme A gene. Two mRNAs encode the same mature granzyme A with different leader peptides. J.Biol. Chem. 267: 25488–93
46. Karlhofer, F. M., W. M. Yokoyama. 1991. Stimulation of murine natural killer (NK) cells by a monoclonal antibody specific for the NK1.1 antigen. IL-2-activated NK cells possess additional specific stimulation pathways. J. Immunol. 146: 3662–73
47. Sentman, C. L., J. Hackett, Jr., V. Kumar, M. Bennett. 1989. Identification of a subset of murine natural killer cells that mediates rejection of Hh-1d but not Hh-1b bone marrow grafts. J. Exp.Med. 170: 191–202
48. Zhang, B. N., T. Yamamura, T. Kondo, M. Fujiwara, T. Tabira. 1997. Regulation of experimental autoimmune encephalomyelitis by natural killer (NK) cells. J. Exp. Med. 186: 1677–87
49. Scalzo, A. A., N. A. Fitzgerald, A. Simmons, A. B. La Vista, G. R. Shellam. 1990. Cmv-1, a genetic locus that controls murine cytomegalovirus replication in the spleen. J. Exp. Med. 171: 1469–83 a) expression of a mouse Ly49A transgene:
b) a deficiency of natural killer activity of at least 50% as measured by reduction in specific lysis of YAC-1, RMA-S, or B16 tumor cells; and
c) a substantially normal complement of other lymphocytes.

2. A transgenic mouse comprising:
i) somatic cells and germ cells comprising a nucleotide sequence encoding a mouse Ly49A inserted into a genomic nucleotide sequence of a mouse granzyme A gene thereby replacing a start codon of the granzyme A gene such that a nucleotide sequence of a start codon of the nucleotide sequence encoding Ly49A is operably linked to a granzyme A promoter such that a mouse Ly49A transgene is expressed, and
ii) a deficiency in T cells.

3. A method of producing a progeny transgenic mouse having:
i) a deficiency of natural kilter activity of at least 50% as measured by reduction in specific lysis of YAC-1, RMA-S, or B16 tumor cells, and
ii) a deficiency in T cells, comprising:
a) mating a first transgenic mouse whose somatic cells and germ cells comprise a nucleotide sequence encoding a mouse Ly49A inserted into a genomic nucleotide sequence of a mouse granzyme A gene thereby replacing a start codon of the granzyme A gene such that a nucleotide sequence of a start codon

What is claimed is:

1. A transgenic mouse whose somatic cells and germi cells comprise a nucleotide sequence encoding a mouse Ly49A inserted into a genomic nucleotide sequence of a mouse granzyme A gene thereby replacing a start codon of the granzyme A gene such that a nucleotide sequence of a start codon of the nucleotide sequence encoding Ly49A is operably linked to a granzyme A promoter, said mouse having:

of the nucleotide sequence encoding Ly49A is operably linked to a granzyme A promoter such that a mouse Ly49A transgene is expressed with a second transgenic mouse, wherein the first transgenic mouse has the deficiency of natural killer activity and a normal complement of other lymphocytes, and wherein the second transgenic mouse has a deficiency in T cells and a normal complement of other lymphocytes; and b) selecting progeny derived from the mating of step a) which has a deficiency of natural killer cells and T cells.

4. A transgenic mouse whose somatic cells and germ cells comprise a nucleotide sequence encoding a mouse Ly49A inserted into the genomic nucleotide sequence of a mouse granzyme A gene thereby replacing a start codon of the granzyme A gene such that a nucleotide sequence of a start codon of the nucleotide sequence encoding Ly49A is operably linked to a granzyme A promoter such that a mouse Ly49A transgene is expressed having:

i) a deficiency of natural killer activity of at least 50% as measured by reduction in specific lysis of YAC-1, RMA-S, or B16 tumor cells, and ii) a deficiency in B cells.

5. A transgenic mouse comprising:

i) somatic cells and germ cells comprising a nucleotide sequence encoding a mouse Ly49A inserted into a genomic nucleotide sequence of a mouse granzyme A gene thereby replacing a start codon of the granzyme A gene such that a nucleotide sequence of a start codon of the nucleotide sequence encoding Ly49A is operably linked to a granzyme A promoter such that a mouse Ly49A transgene is expressed, and ii) a deficiency in B cells.

6. A method of producing a progeny transgenic mouse having:

i) a deficiency of natural killer activity of at least 50% as measured by reduction in specific lysis of YAC-1, RMA-S, or B16 tumor cells, and ii) a deficiency in B cells, comprising:

a) mating a first transgenic mouse whose somatic cells and germ cells comprise a nucleotide sequence encoding a mouse Ly49A inserted into a genomic nucleotide sequence of a mouse granzyme A gene thereby replacing a start codon of the granzyme A gene such that a nucleotide sequence of a start codon of the nucleotide sequence encoding Ly49A is operably linked to a granzyme A promoter such that a mouse Ly49A transgene is expressed with a second transgenic mouse, wherein the first transgenic mouse has the deficiency of natural killer activity and a normal complement of other lymphocytes, and wherein the second transgenic mouse has a deficiency in B cells and a normal complement of other lymphocytes; and b) selecting progeny derived from the mating of step a) which has a deficiency of natural killer cells and B cells.

7. A transgenic mouse comprising:

i) somatic cells and germ cells comprising a nucleotide sequence encoding a mouse Ly49A inserted into a genomic nucleotide sequence of a mouse granzyme A gene thereby replacing a start codon of the granzyme A gene such that a nucleotide sequence of a start codon of the nucleotide sequence encoding Ly49A is operably linked to a granzyme A promoter such that a mouse Ly49A gene is expressed, and ii) a deficiency in T cells; and iii) a deficiency in B cells.

8. A method of producing a progeny transgenic mouse having:

i) a deficiency of natural killer activity of at least 50% as measured by reduction in specific lysis of YAC-1, RMA-S, or B16 tumor cells, and ii) a deficiency in T cells, and iii) a deficiency in B cells, comprising:

a) directing a first mating of a first transgenic mouse whose somatic cells and germ cells comprise a nucleotide sequence encoding a mouse Ly49A inserted into the genomic nucleotide sequence of a mouse granzyme A gene thereby replacing a start codon of the granzyme A gene such that a nucleotide sequence of a start codon of the nucleotide sequence encoding Ly49A is operably led to a granzyme A promoter such that a mouse Ly49A transgene is expressed with a second transgenic mouse, then directing a second mating of the progeny derived form the first mating with a third transgenic mouse, wherein the first transgenic mouse has the deficiency of natural killer activity and a normal complement of other lymphocytes, wherein another of the mice has a deficiency in T cells and a normal complement of other lymphocytes, and wherein the remaining mouse has a deficiency in B cells and a normal complement of other lymphocytes; and b) selecting progeny derived from the second mating which has a deficiency in natural killer cells, T cells and B cells.

9. A method for producing a transgenic mouse containing human tissues, comprising:

a) providing a mouse which has a deficiency of natural killer activity of at least 50% as measured by reduction in specific lysis of YAC-1, RMA-S, or B16 tumor cells, wherein the mouse comprises somatic cells and germ cells comprising a nucleotide sequence encoding a mouse Ly49A inserted into a genomic nucleotide sequence of a mouse granzyme A gene thereby replacing a start codon of the granzyme A gene such that a nucleotide sequence of a start codon of the nucleotide sequence encoding Ly49A is operably linked to a granzyme A promoter such that a mouse Ly49A gene is expressed; and b) transplanting human tissue into the mouse.

10. A method for determining whether a human disease is caused by a pathogenic agent, comprising:

a) providing a mouse which has a deficiency of natural killer activity of at least 50% as measured by reduction in specific lysis of YAC-1, RMA-S, or B16 tumor cells, wherein the mouse comprises somatic cells and germ cells comprising a nucleotide sequence encoding a mouse Ly49A inserted into a genomic nucleotide sequence of a mouse granzyme A gene thereby replacing a start codon of the granzyme A gene such that a nucleotide sequence of a start codon of the nucleotide sequence encoding Ly49A is operably linked to a granzyme A promoter such that a mouse Ly49A transgene is expressed;

b) transplanting non-diseased human tissue into the mouse;

c) contacting diseased human tissue with the non-diseased human tissue; and d) determining whether the non-diseased human tissue acquires the disease.

11. A method of studying natural killer cells comprising:

a) obtaining a NKDef mouse, whose somatic cells and germ cells comprise a nucleotide sequence encoding a mouse Ly49A inserted into a genomic nucleotide sequence of a mouse granzyme A gene thereby replacing a start codon of the granzyme A gene such that the nucleotide sequence encoding Ly49A is operably linked to a granzyme A promoter such that a mouse Ly49A transgene is expressed, and a mouse having wild-type natural killer activity;

b) infecting the NKDef mouse and the mouse having wild-type natural killer activity with a pathogen or with cancer cells; and c) evaluating differences in immunity between the NKDef mouse and the mouse having wild-type activity.

12. Mouse natural killer cells obtained from a mouse whose somatic cells and germ cells comprise a nucleotide sequence encoding a mouse Ly49A inserted into a genomic nucleotide sequence of a mouse granzyme A gene thereby replacing a start codon of the granzyme A gene such that the nucleotide sequence of a start codon of the nucleotide sequence encoding Ly49A is operably linked to a granzyme A promoter such that a mouse Ly49A transgene is expressed, and having a deficiency of interferon γ production of at least 50% when compared to wild-type mouse natural killer cells.

13. A method of studying natural killer cells, comprising comparing natural killer cells from a NKDef mouse, whose somatic cells and germ cells comprise a nucleotide sequence encoding a mouse Ly49A inserted into a genomic nucleotide sequence of a mouse granzyme A gene thereby replacing a start codon of the granzyme A gene such that a nucleotide sequence of a start codon of the nucleotide sequence encoding Ly49A is operably linked to a granzyme A promoter such that a mouse Ly49A transgene is expressed, with the natural killer cells from a mouse having wild-type natural killer activity.

* * * * *

UNITED STATES PATENT AND TRADEMARK OFFICE
CERTIFICATE OF CORRECTION

PATENT NO. : 6,548,737 B1
DATED : April 15, 2003
INVENTOR(S) : Yokoyama et al.

It is certified that error appears in the above-identified patent and that said Letters Patent is hereby corrected as shown below:

Column 1,
Line 36, remove "such as"
Lines 42 and 43, should be in the same paragraph.

Column 2,
Line 5, replace "in vivo" with -- *in vivo* --
Line 11, replace "scid" with -- *scid* --
Line 40, replace "in vitro" with -- *in vitro* --

Column 3,
Line 41, "NK cells should be moved to the DEFECTS column.

Column 4,
Line 20, replace "interferon-y" with -- interferon-γ --

Column 8,
Line 16, replace "CDNA" with -- cDNA --
Line 18, replace "CDNA" with -- cDNA --
Line 19, replace "SalI-Kpnl" with -- *Sal*I-*Kpn*I --
Line 25, replace "in vitro" with -- *in vitro* --
Lines 35 and 54, replace "in vivo" with -- *in vivo* --
Line 37, replace "$^{121}$I-UdR-labeled" with -- $^{125}$I-UdR-labeled --

Column 9,
Line 10, replace "scid" with -- *scid* -- and replace "in vivo" with -- *in vivo* --
Lines 11, 14 and 15, replace "scid" with -- *scid* --
Line 48, replace "in vivo" with -- *in vivo* --
Line 50, replace "*E. coli*" with -- E. coli --
Line 52, replace "mean±SD" with -- mean ±SD --
Line 55, replace "in vitro" with -- *in vitro* --
Line 62, replace "lysis±SD" with -- lysis ±SD --

Column 10,
Line 11, replace "scid-NKDef" with -- *scid*-NKDef --
Line 66, replace "SmaI" with -- *Sma*I --
Line 67, replace "XhoI" with -- *Xho*I --

UNITED STATES PATENT AND TRADEMARK OFFICE
CERTIFICATE OF CORRECTION

PATENT NO. : 6,548,737 B1
DATED : April 15, 2003
INVENTOR(S) : Yokoyama et al.

It is certified that error appears in the above-identified patent and that said Letters Patent is hereby corrected as shown below:

Column 11,
Line 1, replace "SmaI" with -- *Sma*I --
Line 11, replace "SalI" with -- *Sal*I -- and replace "KpnI" with -- *Kpn*I --
Line 33, replace "in" with -- *in* --
Line 34, replace "vitro" with -- *vitro* --
Line 49, replace "the.progeny" with -- the progeny --
Lines 59 and 60, replace "in vitro" with -- *in vitro* --

Column 12,
Line 2, replace "in vivo" with -- *in vivo* -- (two occurrences)
Line 20, "At" should be -- As --
Lines 24 and 41, replace "in vitro" with -- *in vitro* -- and replace "in vivo" with -- *in vivo* --
Line 43, replace "in vivo" with -- *in vivo* --
Line 54, replace "in vitro" with -- *in vitro* --
Lines 65 and 67, replace "scid" with -- *scid* --

Column 13,
Lines 1, 4 and 5, replace "scid" with -- *scid* --
Line 2, replace "in vivo" with -- *in vivo* --
Line 31, replace "in vitro" with -- *in vitro* --
Line 33, add -- . -- after "shown)"
Line 55, replace "NK1.1$^+$ CD3$^-$" with -- NK1.1$^+$CD3$^-$ --
Line 59, replace "in" with -- *in:* --
Line 60, replace "vitro" with -- *vitro* --

Column 15,
Line 18, replace "interferon-y" with -- interferon-γ --

Column 16,
Lines 24, 31, 32, 33, 34 and 35, replace "scid" with -- *scid* --
Lines 38, 39, 41 and 56, replace "scid" with -- *scid* --

UNITED STATES PATENT AND TRADEMARK OFFICE
CERTIFICATE OF CORRECTION

PATENT NO.    : 6,548,737 B1
DATED         : April 15, 2003
INVENTOR(S)   : Yokoyama et al.

It is certified that error appears in the above-identified patent and that said Letters Patent is hereby corrected as shown below:

Column 17,
Line 28, replace "in vitro" with -- *in vitro* --
Line 49, replace "C57BL/6-Prkdcscid/Sz" with -- C57BL/6-Prkdc*scid*/Sz --
Line 51, replace "Me." with -- ME --
Line 52, replace "Mo." with -- MO --
Line 55, replace "Md." with -- MD --
Line 61, replace "Calif." with -- CA --
Line 62, replace "N.Y." with -- NY --
Line 64, replace "Ind." with -- IN --

Column 18,
Line 5, replace "mabs" with -- mAbs --
Line 6, replace "Calif." with -- CA --
Line 15, replace "Pa." with -- PA --
Line 19, replace "Calif." with -- CA --
Line 20, replace "*Escherichia coli*" with -- Escherichia coli --
Line 22, replace "Mo." with -- MO --
Line 23, replace "N.Y." with -- NY --
Line 30, replace "Calif." with -- CA -- and replace "in vivo" with -- *in vivo* --
Line 39, "NaeI-SmaI" should be -- *Nae*I-*Sma*I --
Line 40, replace "NaeI-SmaI" with -- *Nae*I-*Sma*I --
Lines 43 and 44, replace "1D 70:1" with -- ID NO:1 --
Line 45, replace "XhoI" with -- *Xho*I --
Line 46, replace "SmaI" with -- *Sma*I --
Line 48, replace "SalI-KpnI" with -- *Sal*I-*Kpn*I --

Column 19,
Line 36, replace "In vitro" with -- *In vitro* --
Line 43, replace "Ill." with -- IL --
Line 63, replace "in vivo" with -- *in vivo* --

Column 20,
Line 1, replace "Ill." with -- IL --
Line 16, replace "scid" with -- *scid* --
Lines 18 and 19, replace "in vivo" with -- *in vivo* --

UNITED STATES PATENT AND TRADEMARK OFFICE
CERTIFICATE OF CORRECTION

PATENT NO. : 6,548,737 B1
DATED : April 15, 2003
INVENTOR(S) : Yokoyama et al.

It is certified that error appears in the above-identified patent and that said Letters Patent is hereby corrected as shown below:

Column 21,
Line 3, replace "Calif." with -- CA --
Lines 15 and 17, replace "in vivo" with -- *in vivo* --
Line 21, replace "Mass." with -- MA --
Line 26, replace "In vitro" with -- *In vitro* --
Line 35, replace "Mo." with -- MO --
Line 44, "FICT-conjugated" should be -- FITC-conjugated --
Lines 55 and 56, replace "in vitro" with -- *in vitro* --
Lines 65 and 66, replace "scid" with -- *scid* --

Column 22,
Lines 1, 3 and 9, replace "scid" with -- *scid* --
Line 5, replace "scid" with -- *scid* -- (two occurrences)
Line 8, replace "scid-NKDef " with -- *scid*-NKDef --
Line 47, replace "in vivo" with -- *in vivo* --
Line 51, replace "(scid)" with -- (*scid*) --

Column 23,
Line 11, replace "scid" with -- *scid* --
Line 15, replace "C.Solari" with -- C. Solari --
Line 37, replace "S.Winandy" with -- S. Winandy --
Line 61, replace "M.Miyasaka" with -- M. Miyasaka --

Column 24,
Line 18, replace "(scid)" with -- (*scid*) --
Line 24, replace "SCID-hu" with -- *SCID*-hu --
Line 60, replace "alphaand" with -- alpha and --

Column 25,
Line 11, replace "J.Biol." with -- J. Biol. --
Line 21, replace "Exp.Med." with -- Exp. Med. --
Line 61, replace "germi" with -- germ --

UNITED STATES PATENT AND TRADEMARK OFFICE
CERTIFICATE OF CORRECTION

PATENT NO.    : 6,548,737 B1
DATED         : April 15, 2003
INVENTOR(S)   : Yokoyama et al.

It is certified that error appears in the above-identified patent and that said Letters Patent is hereby corrected as shown below:

<u>Column 26,</u>
Line 20, replace "kilter" with -- killer --

<u>Column 28,</u>
Line 10, replace "led" with -- linked. --
Line 14, replace "form" with -- from --

<u>Column 30,</u>
Line 1, add -- - -- between "interferon" and "γ"

Signed and Sealed this

Fifteenth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,548,737 B1 Page 1 of 1
DATED : April 15, 2003
INVENTOR(S) : Yokoyama et al.

It is certified that error appears in the above-identified patent and that said Letters Patent is hereby corrected as shown below:

<u>Title page,</u>
Item [75], Inventors: "Wayne M. Yokoyana" should read -- Wayne M. Yokoyama --

Signed and Sealed this

Fourth Day of November, 2003

JAMES E. ROGAN
*Director of the United States Patent and Trademark Office*

SEQUENCE LISTING

<160> NUMBER OF SEQ ID NOS: 2

<210> SEQ ID NO 1
<211> LENGTH: 22
<212> TYPE: DNA
<213> ORGANISM: Artificial
<220> FEATURE:
<221> NAME/KEY: primer_bind
<222> LOCATION: (1)..(22)
<223> OTHER INFORMATION: Primer

<400> SEQUENCE: 1
cctgaagcat gctatctcac ga                                          22

<210> SEQ ID NO 2
<211> LENGTH: 26
<212> TYPE: DNA
<213> ORGANISM: Artificial
<220> FEATURE:
<221> NAME/KEY: primer_bind
<222> LOCATION: (1)..(26)
<223> OTHER INFORMATION: Primer

<400> SEQUENCE: 2
gttcccgggc tctcccaccc caatca                                      26